(12) United States Patent
Bennet et al.

(10) Patent No.: US 12,102,997 B2
(45) Date of Patent: Oct. 1, 2024

(54) SAFE SPECIMEN TRANSPORTATION ISOLATION CONTAINER

(71) Applicant: ARIZONA BOARD OF REGENTS ON BEHALF OF THE UNIVERSITY OF ARIZONA, Tucson, AZ (US)

(72) Inventors: Devasier Bennet, Phoenix, AZ (US); Frederic Zenhausern, Phoenix, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 18/007,456

(22) PCT Filed: Jul. 30, 2021

(86) PCT No.: PCT/US2021/043905
§ 371 (c)(1),
(2) Date: Jan. 30, 2023

(87) PCT Pub. No.: WO2022/026831
PCT Pub. Date: Feb. 3, 2022

(65) Prior Publication Data
US 2023/0347335 A1 Nov. 2, 2023

Related U.S. Application Data

(60) Provisional application No. 63/059,404, filed on Jul. 31, 2020.

(51) Int. Cl.
*B01L 3/00* (2006.01)
*A01N 1/02* (2006.01)
(Continued)

(52) U.S. Cl.
CPC .............. *B01L 3/502* (2013.01); *A01N 59/04* (2013.01); *A01P 1/00* (2021.08); *A61B 5/097* (2013.01);
(Continued)

(58) Field of Classification Search
CPC ............ B01L 3/502; B01L 2200/0678; B01L 2200/185; B01L 2300/042;
(Continued)

(56) References Cited

U.S. PATENT DOCUMENTS 5,267,791 A * 12/1993 Christian ................ B01F 35/50
422/910
8,491,855 B2 * 7/2013 Yong .................. A61B 10/0045
422/547

(Continued)

*Primary Examiner* — Luan K Bui
(74) *Attorney, Agent, or Firm* — Leydig, Voit & Mayer, Ltd.

(57) ABSTRACT

Provided herein are portable biocontainment devices for safe and reliable collection of biological samples, including liquid and gas samples. A sample inlet for collecting fluids and/or gases, including oral fluids and expired breath samples, is connected to a container having a climate-controlled container reservoir. One or more sample containers are connected to the sample inlet for collection of samples. The devices are configured for safe transport and handling of samples, while maintaining sample viability, including for relatively long transport periods. Safety components integrated within the device facilitates safe and effective decontamination of contagious samples. In this manner, aborting the sample preservation by decontamination prior to a hazardous release is achieved within the same apparatus.

22 Claims, 7 Drawing Sheets

(51) Int. Cl.
    *A01N 59/04*    (2006.01)
    *A01P 1/00*    (2006.01)
    *A61B 5/097*    (2006.01)
    *A61B 10/00*    (2006.01)
    *A61L 2/00*    (2006.01)
    *A61L 2/24*    (2006.01)
    *A61L 101/02*    (2006.01)

(52) U.S. Cl.
CPC ...... *A61B 10/0051* (2013.01); *A61B 10/0096* (2013.01); *A61L 2/0023* (2013.01); *A61L 2/24* (2013.01); *A61L 2101/02* (2020.08); *A61L 2202/14* (2013.01); *A61L 2202/18* (2013.01); *B01L 2200/0678* (2013.01); *B01L 2200/185* (2013.01); *B01L 2300/042* (2013.01); *B01L 2300/0681* (2013.01); *B01L 2300/069* (2013.01); *B01L 2300/14* (2013.01); *B01L 2300/1894* (2013.01)

(58) Field of Classification Search
CPC ....... B01L 2300/0681; B01L 2300/069; B01L 2300/14; B01L 2300/1894; A01N 1/0273; A01N 59/04; A01P 1/00; A61B 5/097; A61B 10/0051; A61B 10/0096; A61L 2/0023; A61L 2/24; A61L 2101/02; A61L 2202/14; A61L 2200/18; C12N 2521/00; C12N 2523/00; C12M 99/00
USPC ...................... 422/187, 400, 401, 547; 206/6
See application file for complete search history.

(56) References Cited

U.S. PATENT DOCUMENTS

| | | | | |
|---|---|---|---|---|
| 2005/0281713 | A1* | 12/2005 | Hampsch | A61B 5/150351 422/400 |
| 2006/0039833 | A1* | 2/2006 | Yong | B01L 3/502 73/864.91 |
| 2010/0329944 | A1* | 12/2010 | Hassan | B01J 19/1862 422/187 |
| 2011/0097250 | A1* | 4/2011 | Yong | B01L 3/5055 422/547 |
| 2013/0125564 | A1* | 5/2013 | Booth | B01D 8/00 62/55.5 |
| 2013/0306913 | A1* | 11/2013 | Li | C10B 47/06 422/162 |
| 2014/0243204 | A1* | 8/2014 | Sparg | A01N 25/18 422/187 |

\* cited by examiner

```
                    ┌──────────────┐
            400 ──  │ Providing a  │
                    │  Portable    │
                    │Biocontainment│
                    │   Device     │
                    └──────┬───────┘
                ┌──────────┴──────────┐
                ▼                     ▼
┌─────────────────────┐         ┌─────────────────────┐
│Introducing Liquid-  │         │Introducing Gas-Phase│ ── 406
│ Phase Biological    │  and    │ Biological Sample   │
│      Sample         │         │                     │
└──────────┬──────────┘         └──────────┬──────────┘
 402                                       ▼
                                 ┌─────────────────────┐
                                 │  Condensing Gas-    │ ── 408
                                 │ Phase Sample to     │
                                 │ Condensed Liquid    │
                                 │      Sample         │
                                 └──────────┬──────────┘
           ▼                                ▼
┌─────────────────────┐         ┌─────────────────────┐
│Collecting the Liquid│         │   Collecting the    │ ── 410
│- Phase Biological   │         │  Condensed Liquid   │
│      Sample         │         │      Sample         │
└──────────┬──────────┘         └──────────┬──────────┘
 404                                       │
            └──────────┬───────────────────┘
                       ▼
              ┌ ─ ─ ─ ─ ─ ─ ─ ─ ┐
       412 ── │   Cooling the   │
              │   Sample(s)     │
              └ ─ ─ ─ ─┬─ ─ ─ ─ ┘
                       ▼
              ┌─────────────────┐
              │ Storing One or  │
       414 ── │   More Viable   │
              │Biological Samples│
              └─────────────────┘
```

FIG. 4A

```
          ┌─────────────────┐
   414 ──→│  Storing One or │
          │   More Viable   │
          │Biological Samples│
          └─────────────────┘
                   │
   452             ▼
  ┌─ ─ ─ ─ ─ ─ ─┐  ┌─────────────────┐
  │Shipping Performed│  │Shipping the One or│ ── 450
  │by a Commercial│→ │More Viable Biological│
  │Service and/or│  │Samples to a Remote│
  │Drone Delivery│  │ Testing Facility │
  └─ ─ ─ ─ ─ ─ ─┘  └─────────────────┘
                           │
                           ▼
          ┌──────────────────────────────────┐
          │Monitoring Shipping Conditions during transit.│
          │     Including one or more of:    │── 454
          │  Time; Temperature; Impact Force │
          │       Humidity; Pressure         │
          └──────────────────────────────────┘
```

Monitoring Shipping Conditions during transit. Including one or more of: Time; Temperature; Impact Force Humidity; Pressure — 454

Within Shipping Conditions → 456 Delivered Samples are in Condition for Retrieval/Analysis Exceed Shipping Conditions and/or Contamination Detected → 458 Implementing Device Decontamination

FIG. 4B

SAFE SPECIMEN TRANSPORTATION ISOLATION CONTAINER

CROSS-REFERENCE TO RELATED APPLICATIONS

This application is a U.S. National Stage Application filed under 35 U.S.C. § 371 of International Application No. PCT/US2021/043905, filed Jul. 30, 2021, which claims the benefit of U.S. Provisional Application No. 63/059,404, filed on Jul. 31, 2020, each of which are incorporated by reference herein in their entirety.

BACKGROUND OF INVENTION

Provided herein are devices that are useful for collecting biological samples, and related methods of safely collecting, storing and transporting samples, including biological samples where viability of the sample can be maintained for subsequent analysis and testing.

In the event of a disaster response, including a pandemic infection, there is a need for biological specimen collection from individuals who may be exposed to an infectious or otherwise dangerous agent. The collected specimen, including a biological specimen, is then sent to a facility for testing. The testing facility may be on-site or may be remote. One of the major bottlenecks in response to a pandemic, however, lies at the specimen collection step, especially for highly infectious respiratory viruses. The collection bottleneck includes collection by healthcare providers within an emergency room at hospitals, within first responder sites, or at a centralized sample collection site. Part of the bottleneck relates to ensuring the sample collectors and handlers remain safe while maintaining the ability to subsequently test collected sample for the agent of interest.

To overcome exposure and provide a safer environment to the care provider, requirements for sample collection include: safe for biohazard disposition or compatible for incineration; easy use for multiple types of biospecimen collection (e.g. breath, saliva, blood); readily purified to preserve the specimen integrity; free from contamination; filter biocontaminants (e.g. bacteria, viruses, particles); easy and safe handling; and free from inactivation. The collected sample should be configured for compatibility with direct shipping safely to remote labs for running analytical tests (e.g. molecular diagnostics by mass spectrometry, gas chromatography, sequencing, PCR, and the like).

Conventional biological specimen collection devices also suffer from lack of safety features in the event of device failure. For example, it would be beneficial to incorporate decontaminants into a collection device for use with device failure to avoid a biohazard exposure, including an infectious agent, to the external environment. Examples of decontaminants include: (1) gamma, X-ray, and electron beam (radiation-based decontamination), (2) ethylene oxide (gas-based decontamination), and (3) high temperature water (steam-based decontamination). Each of those decontaminant has disadvantages, e.g., toxic irradiation, gases often leave a toxic residue, and high temperatures, and are not suitable for portable decontamination devices. There is currently no reliable platform available in a portable device to safely decontaminate pathogens (e.g. SARS-CoV-2, Tier 1 pathogens . . . ) in different environments.

The devices and methods provided herein address these needs by providing a safe and easy to use collection system that is compatible with gas and liquid samples, while ensuring the storage is safe and robust, all while maintaining viability of biological organisms in the stored sample.

SUMMARY OF THE INVENTION

Provided herein is a self-contained two-in-one direct access container for collection of both liquid (e.g., oral fluid (OF)) and gas (e.g., exhaled breath (EB)) samples, including a portable biocontainment apparatus for the self-collection, processing and safe transport of biospecimen from infected individuals. The two-in-one container may be for biocontainment of a sample having a biological material of interest, including a biohazardous material or biological material where biological viability is desired. The two-in-one container optionally has a decontamination component for providing safe and reliable decontamination or sterilization, thereby providing an added layer of safety. In this manner, the portable biocontainment devices provided herein may be characterized as a decontamination disposable container.

Applications include for an infection pandemic response, where first responders and healthcare providers require the capability for the safe collection and movement of infected materials with a highly contagious biological organism from the patients without exposure by using an isolation system. The currently available options do not fully meet the requirement for self-collecting multiple types of biospecimen (e.g. saliva, expelled gas, volatile gas condense, blood or nasal swab) from people, conditioning the specimen for collection or pre-processing into a tube with reagent mixtures and biocontainment for transportation by a vehicle or user to a safe laboratory setting.

Devices provided herein can operate under negative pressure by evacuating air from the system or can operate at ambient pressure. The devices are also suitable for operations in low resource settings or remote areas because of a minimum requirement for manual operation by an unskilled user.

Devices provided herein also integrate safety measures in the event of a potential failure to operate appropriately, including from adverse physical events that could result in breakage of one or more components. For this purpose, aborting the sample preservation by decontaminating it prior to an uncontrolled potentially hazardous release is compatible within the same apparatus. The present technology is compatible with release of a decontaminant into the device in the event of failure to decontaminate biological samples and reduce the risk of biohazardous biological samples entering the external environment. The technology described herein is compatible with a range of decontaminants. One example is a decontaminant that is supercritical fluid carbon dioxide ($scCO_2$), which is considered a 'green' and sustainable technology because it does not leave toxic residues. Additionally, $scCO_2$ is a safe and effective decontaminant of highly contagious pathogens. See, e.g., Bennet et al., *Evaluation of Supercritical $CO_2$ Sterilization Efficacy for Sanitizing Personal Protective Equipment from the Coronavirus SARS-CoV-2*, Elsevier, 18 Mar. 2021. A disinfectant additive may be mixed with the $scCO_2$.

To achieve the above-referenced advantages, as well as other advantages, and in accordance with the purpose of the technology, an embodiment of the invention comprises a portable biocontainment device for collecting and storing a hazardous or an infectious agent comprising: a container having a side wall, a bottom wall and a top wall to define a container reservoir; a fluid port traversing the side wall of the container and extending between the container reservoir and an external environment outside the container reservoir.

The fluid port comprises one or more openings configured to receive a liquid-phase biological sample and/or a gas-phase biological sample; a gas biological sample inlet; and a liquid biological sample inlet; wherein the one or more openings are externally positioned relative to the container reservoir and each of the gas biological sample inlet and the liquid biological sample inlet is positioned in the container reservoir. A condensing spiral tube is positioned in the container reservoir. The condensing spiral tube has a spiral tube proximal end fluidically connected to the gas biological sample inlet. A condensation sample container is fluidically connected to a distal end of the condensing spiral tube for storing the condensed liquid sample from the gas-phase biological sample. The fluidic connection may be via a direct connection, or may be by an indirect connection, with an intervening component, such as a condensate collector. A tube is positioned in the container reservoir and has a tube proximal end fluidically connected to the liquid biological sample inlet. A liquid sample container is fluidically connected to a distal end of the tube for storing a liquid sample from the liquid-phase biological sample.

Examples of the hazardous or the infectious agent, including portions thereof, include but are not limited to, polynucleotides, proteins, polypeptides, antibodies, including presence or absence thereof and specific sequences thereof.

The device is compatible with any number of sample containers and/or tubes, as desired. The tubes are configured to convey a fluid sample, such as a liquid sample and/or a gas sample. Accordingly, there may be more than one condensation sample container and more than one liquid sample container. This is especially useful where a tester of the biological sample may use different containers for different tests, and for applications requiring sufficient biological sample to run multiple tests. It is also useful where there may be more than one tester or more than one testing facility.

In embodiments, the portable biocontainment device further comprises a cooling chamber positioned in the container reservoir and is configured to receive a cooling element. The cooling chamber is in thermal contact with the condensing spiral tube. In aspects of the technology, the cooling chamber is in thermal contact with other components of the device, including the condensation sample container and the liquid sample container, particularly for embodiments where the sample containers are desirably cooled.

In another aspect of the technology, the top wall of the container is a removable cap that is configured for removal to position the cooling element in the cooling chamber and/or to connect the portable biocontainment device to a biocontainment handling component for biocontainment during sample handling. To further facilitate safe transportation of the device, in embodiments, the removable cap may be irreversibly attached to the device, including through the use of fasteners and/or adhesive. For example, a fastener may be a plurality of screws that fasten the cap to the container.

In one embodiment, the one or more openings comprise a gas-phase opening and a liquid-phase opening, further comprising: an insertable liquid collector; an insert port extending between the liquid-phase opening and the liquid biological sample inlet, wherein the insert port is configured to receive the insertable liquid collector.

In further aspects of the technology, the insertable liquid collector comprises: a compressible absorbent pad having a longitudinal axis extending between a first end and a second end; a liquid indicator aligned with the compressible absorbent pad longitudinal axis; a hand bar, having a proximal end connected to the compressible absorbent pad second end and/or the liquid indicator; wherein the compressible absorbent pad is configured for insertion into the insert port and the hand bar is accessible to a subject to control compression of the compressible absorbent pad in the insert port.

In another embodiment, the insertable liquid collector comprises: a compressible absorbent pad having a longitudinal axis extending between a first end and a second end; a removable liquid collection conduit, having a distal end configured to fluidically connect to the liquid biological sample inlet; a liquid indicator aligned with the compressible absorbent pad longitudinal axis; a hand bar, having a proximal end connected to the compressible absorbent pad second end and/or the liquid indicator; a plurality of apertures positioned through the insert port for conveying liquid sample from the gas-phase opening to the liquid biological sample inlet; wherein the compressible absorbent pad is configured for insertion into the removable liquid collection conduit and the hand bar is accessible to a subject to control compression of the compressible absorbent pad in the insert port. Of course, the removable liquid collection conduit may be first attached to the insertable liquid collector or, alternatively, the removable liquid collection conduit may be first inserted into the insert port.

In one embodiment, the portable biocontainment device further comprises an excess liquid collection container connected to the fluid port to collect excess liquid from the introduced liquid-phase biological sample. The excess liquid collection container is positioned so that it may receive excess liquid-phase biological sample from the gas-phase opening, the liquid-phase opening, as well as the apertures on the insert port. Of course, there may be more than one excess liquid container which would be useful in instances where the user overestimates the portable biocontainment device's liquid volume capacity.

In still another aspect of the technology, the portable biocontainment device is configured for safe transportation of a biohazardous sample under a range of ambient environmental conditions and/or a range of transport times, including up to 28 hours.

In embodiments, the container reservoir is pressurizable to a negative pressure. In some aspects of the technology, the negative pressure is generated in the container reservoir by a pressure pump assembly operably connected to the container reservoir. In one embodiment, the pressure pump assembly comprises: a spring to remove air from the container reservoir, a vent between the container reservoir and external environment having an open vent configuration for air removal from the container reservoir during pump operation and a close vent configuration to maintain the negative pressure in the container reservoir, and a filter between the container reservoir and the external environment to prevent release of a biological agent to the external environment.

In one embodiment, the liquid sample container has a container volume to accommodate a liquid sample volume less than or equal to 3 mL, and the condensation sample container has a container volume to accommodate a condensed liquid sample volume less than or equal to 3 mL.

In further aspects of the technology, the liquid biological sample inlet receives an oral fluid, such as saliva, and/or the gas biological sample inlet receives an exhaled breath from a patient to be tested for a symptom of the infectious agent, including a biomarker of the infectious agent. Those inlets may be the same, where an individual can exhale gas and saliva into a single opening that acts as both the liquid and gas biological sample inlet. Alternatively, the inlets may be physically distinct. Alternatively, the inlets may be a combination thereof, with a common gas and liquid inlet plus another inlet to accommodate a liquid collection element, such as an absorbent pad, to facilitate liquid collection, handling and delivery to desired portions of the device.

In another embodiment, the portable biocontainment device further comprises a filtration system positioned between the liquid biological sample inlet and the tube to filter the liquid-phase biological sample.

In one embodiment, during biocontainment storage, the infectious agent in the liquid sample container and/or the condensation sample container remains viable. This is particularly useful where subsequent tests require a viable infectious agent in the sample.

In another aspect of the technology, a collected sample may be used for any one or more of: biomarker analysis from a biological fluid sample, including saliva, sputum, plasma, blood, urine, amniotic fluid, bone marrow, breast milk, synovial fluid, semen, vaginal fluid, mucus, or lymph; exhaled breath biomarker analysis; noninvasive based dehydration marker analysis; microbiota analysis; dehydration analysis; respiratory infection markers analysis; environmental exposure to a chemical, biological, radiological, nuclear and/or explosive (CBRNE) agent; or a diagnostic assay at a remote facility for detecting one or more of a virus, bacteria, fungus and/or a polynucleotide sequence (e.g., DNA and/or RNA).

In one embodiment, the portable biocontainment device further comprises a targeted decontamination device operably connected to the container comprising: one or more disinfectant lines having a disinfectant line proximal end and a disinfectant line distal end; one or more disinfectant storage containers operably connected to the disinfectant line proximal end, wherein at least one of the one or more disinfectant storage containers is configured to store $CO_2$; a controller connected to the one or more disinfectant lines to control a flowrate of a disinfectant from the one or more disinfectant storage containers through the one or more disinfectant lines; a pressure vessel, operably connected to the disinfectant line distal end, defining a pressure vessel volume, wherein the liquid sample container and the condensation sample container are positioned within the pressure vessel volume; a controllable heating element positioned within the pressure vessel volume; a pressure sensor operably connected to the pressure vessel; an exhaust line having an exhaust line proximal end and an exhaust line distal end wherein the pressure vessel is operably connected to the exhaust line proximal end and the exhaust line distal end opens to the external environment; an exhaust controller connected to the exhaust line to control a flowrate of gas from the pressure vessel volume to the external environment; wherein the pressure vessel is configured to contain elevated pressure levels and temperatures to ensure $CO_2$ transformation to supercritical $CO_2$ ($scCO_2$) for sufficient time period to disinfect any relevant biohazard, such as a contagion. Representative ranges include up to 2500 psi and temperature levels up to 60° C. for a period of between 10 minutes to 60 minutes. This facilitates $CO_2$ transformation to $scCO_2$ in the pressure vessel volume, and related device components, to sterilize any contagion accessible to the $scCO_2$.

In another embodiment, the portable biocontainment device further comprises a non-targeted decontamination device operably connected to the container comprising: one or more disinfectant lines having a disinfectant line proximal end and a disinfectant line distal end; one or more disinfectant storage containers operably connected to the disinfectant line proximal end wherein at least one of the one or more disinfectant storage containers is configured to store $CO_2$; a controller connected to the one or more disinfectant lines to control a flowrate of a disinfectant from the one or more disinfectant storage containers through the one or more disinfectant lines; a controllable preheating element wherein at least a portion of the one or more disinfectant lines traverses the controllable preheating element to heat the disinfectant flowing through the one or more disinfectant lines; the one or more disinfectant lines distal end configured to open to the container reservoir; a pressure sensor operably connected to the container reservoir; an exhaust line having an exhaust line proximal end and an exhaust line distal end wherein the container reservoir is operably connected to the exhaust line proximal end and the exhaust line distal end opens to the external environment; an exhaust controller connected to the exhaust line to control a flowrate of gas from the container reservoir to the external environment; wherein the side wall, the bottom wall and the top wall of the container are configured to contain pressure levels up to 2500 psi and temperature levels up to 60° C. for a period of between 10 minutes to 60 minutes configured for the $CO_2$ transformation to supercritical $CO_2$ ($scCO_2$) in the container reservoir to sterilize any contagion accessible to the $scCO_2$.

In further aspects of the technology, at least one of the one or more disinfectant storage containers is configured to store a disinfectant additive. In this manner, the controller may also control a flowrate of the disinfectant additive through the one or more disinfectant lines. In these embodiments, the $scCO_2$ and the disinfectant additive work together to sterilize any contagion accessible to the $scCO_2$ and the disinfectant additive.

Also provided herein are methods of collecting, storing, and transporting viable, volatile, and semi-volatile biological samples using any of the devices provided herein. For example, in one embodiment, a method of storing one or more viable biological samples may comprise: providing a portable biocontainment device where the portable biocontainment device may be one of any of the devices provided herein; introducing: the liquid-phase biological sample into the liquid biological sample inlet and the gas-phase biological sample into the gas biological sample inlet; collecting: the liquid-phase biological sample into the liquid sample container; condensing at least a portion of the gas-phase biological sample in the condensing spiral tube to the condensed liquid sample; collecting the condensed liquid sample into the condensation sample container; thereby storing one or more viable biological samples.

In one embodiment, the method may include introducing the cooling element to the cooling chamber and cooling the liquid sample container and the condensation sample container and/or collection components with the introduced cooling element.

In one embodiment, the method may further comprise shipping the collected one or more viable biological samples to a remote testing facility. In one embodiment, the shipping may be by a commercial service and/or drone delivery.

In one embodiment, the method may include the one or more viable biological samples remaining viable and safely contained for a shipping condition. The shipping condition may be selected from the group consisting of: a shipping time period of up to 28 hours and up to 4 days with a stabilizer in the sample container; a temperature variation ranging from −60° C. to 60° C., with the temperature of the sample container selectably controlled depending on the one or more viable biological samples, wherein the one or more viable biological samples comprise of one or more of a protein, a lipid, a volatile organic compound, or microbiota; an impact or shock force against the portable biocontainment device; and a humidity range of between 1% to 100% humidity. The relatively wide ranges of physical parameters reflect that the devices provided herein are compatible with a wide range of times, temperatures and/or humidity. For example, if biological viability is desired, the device may have an internal temperature relevant to maintain viability, such as around room to body temperature (e.g., 20° C. to 40° C.). If the samples are desirably frozen, the temperature may be maintained at or below freezing (e.g., below 0° C.). If a vacuum is desired in the container to further decrease risk of release to the surrounding environment, the pressure may be less than atmospheric, including at sea level of less than 1 atmosphere, and with little or no humidity outside of the sample containers and lines. If there is a leak, the pressure and/or humidity may increase, with an attendant risk of exposure. In that situation, the sensor may be used to indicate a potentially out of range characteristic. A user (manual) or controller (automatically) may then initiate decontamination with a decontamination device.

Further provided herein are methods for decontaminating a contagious material. In one embodiment, the method comprises the steps of: providing a portable biocontainment device where the portable biocontainment device may be one of any of the devices provided herein; collecting the contagious material to be decontaminated into the portable biocontainment device; introducing the $CO_2$ to the portable biocontainment device; adjusting the pressure and temperature within the portable biocontainment device to at least 1500 psi and 31° C. to 60° C., respectively, for supercritical transformation of the $CO_2$; and maintaining the pressure and temperature levels for 10 to 60 minutes; thereby decontaminating the contagious material. In some embodiments, the contagious material comprises a pathogen to be sterilized.

In one embodiment, the method may further comprise introducing the disinfectant additive to the portable biocontainment device. For example, the introduction step may be facilitated by the controller in devices where the disinfectant additive is stored in the one or more disinfectant storage containers. In other examples, the introduction step may also be facilitated by introducing the disinfectant additive in a dehydrated form, such as a dissolvable tablet or dried onto a membrane, to the area to be decontaminated. In even further examples, the introduction step may be facilitated by introducing the disinfectant additive in the dehydrated form to the one or more disinfectant lines to be dissolved by the $CO_2$ or $scCO_2$ as the $CO_2$ or $scCO_2$ flow through the one or more disinfectant lines.

In further embodiments, the method further comprises decontaminating the contagious material occurring prior to any hazardous release for medical and or nonmedical applications.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 4A is a flow-chart summary of a method of collecting and securing one or more viable biological samples. FIG. 4B is a flow-chart summary of a method of safely transporting the one or more viable biological samples to a remote testing facility or implementing decontamination procedures if contamination is of concern.

DETAILED DESCRIPTION OF THE INVENTION

Figure 1A:
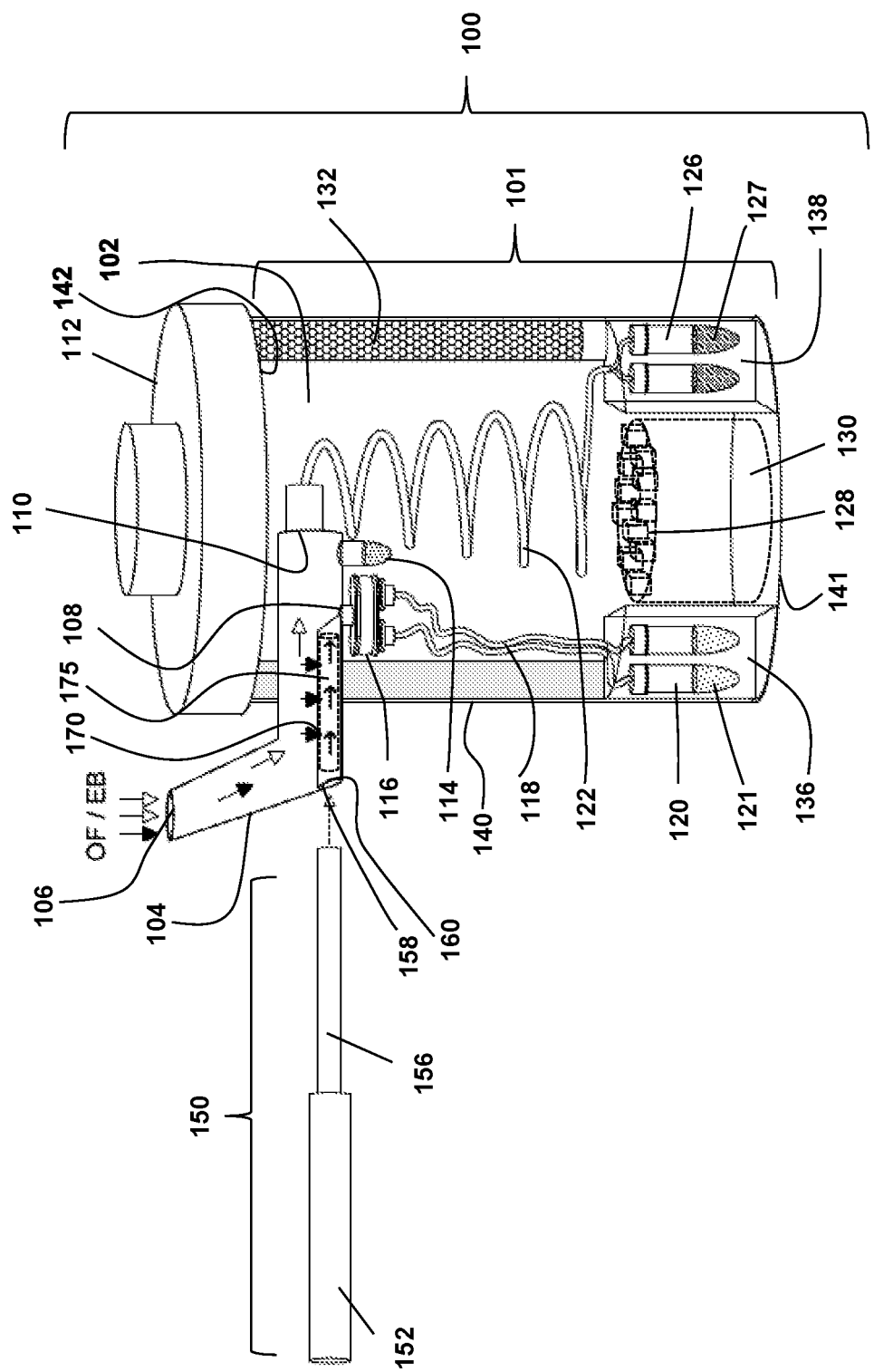
FIG. 1A illustrates a portable biocontainment direct-access device for collecting and storing a hazardous or an infectious agent. The device is a two-in-one disposable device design configured for ambient operation.

In the following description, numerous specific details of the devices, device components and methods of the present invention are set forth in order to provide a thorough explanation of the precise nature of the invention. It will be apparent, however, to those of skill in the art that the invention can be practiced without these specific details.

In general, the terms and phrases used herein have their art-recognized meaning, which can be found by reference to standard texts, journal references and contexts known to those skilled in the art. The following definitions are provided to clarify their specific use in the context of the invention.

"Portable biocontainment device" refers to a system that can collect a biological sample, including from a patient, and store it in a safe manner for transport and handling, including to a remote testing facility. The transport may include by drone delivery, particularly in view of the robustness and containment safety of the biocontainment device. Preferably, the biocontainment device retains viability, so that the sample received at a remote testing remains viable, even after a long transit time under a range of environmental conditions. "Portable" refers to the device that can be hand-carried to receive a sample and for shipment. As desired, the biocontainment device may be handled without any additional packaging, or may be inserted into a separate container for shipping, including any of the storage containers provided in PCT Pub. No. WO 2020/118085 titled "Smart Storage Container for Health Logistics". The portable biocontainment device may be disposable or reusable, including components thereof. For example, the sample containers can be replaced, with at least a portion of the remaining components reused, including components that are reliably disinfected such as by the $scCO_2$ or the $scCO_2$ and disinfectant composition. Other replaceable components may include fluid inlets, fluid ports, fluid lines, or any other component that is not readily disinfectable. In further examples, the portable biocontainment device may be disposed before or after decontamination by disposing the device with proper disposal components, such as biohazard bags and other biohazard receptacles. In some instances, the portable biocontainment device may be autoclaved before disposal or reuse. The device can be characterized as "direct access" because a user can directly access the samples, including via an access panel(s) or door(s) through the container and/or the individual providing the samples can directly access the container for sample storage without needing a technician or medical personnel.

"Operably connected" refers to the configuration of two components that connect, either directly or indirectly, but in a manner that maintains operability and functionality of each component. "Fluidically connected" refers to a configuration of two components for passage of a fluid such as a gas or a liquid, but in a manner that maintains operability and functionality of the individual components.

"Biological sample" includes liquid, gas, volatile, and/or semi-volatile specimens derived from a human, animal, insect, plant, microbe, or any other entity capable of life. Biological samples include, but are not limited to, saliva, sputum, plasma, blood, urine, amniotic fluid, bone marrow, breast milk, synovial fluid, semen, vaginal fluid, mucus, lymph, or exhaled breath.

"Analyte" and "constituent of interest" refer to a substance that is of interest in an analytical procedure and is typically found in a sample introduced to the device, including either gas and/or liquid phase. Analytes of interest may include organic compounds, inorganic compounds, proteins, biomarkers, antibodies, antigens, lipids, polypeptides, polynucleotides, nucleic acids, bacteria, viruses, microbiota, fungi, and parasites.

"Fluid" includes a liquid, a gas, any other substance that does not have a fixed shaped that yields to applied forces and pressures, and any combination thereof. For example, a fluid may be an oral fluid, such as saliva or sputum. A fluid may also be a gas, such as an exhaled breath. Such fluid is particularly compatible with collection applications from a person's mouth, including a combination of breath exhalation and saliva release.

"External environment" refers to the environment, including physical, chemical, and biological conditions, outside of the components of the devices described herein. For example, the environment in which the device is located. This may be the environment during which the sample is being collected (e.g., individual proving sample), transport (e.g., from the collection site to a testing site), and at the test site (when an authorized individual accesses the samples. The devices provided herein are specially configured to minimize risk of release of a hazardous agent to the external environment, whether that is during the original sample collection, sample transport, or providing the sample to a test facility. In this manner, the sample is referred as being "contained" or "safely contained" if the sample remains in the collection sample containers without any leakage outside the sample container, and certainly not any leakage to the external environment.

"Collection components" refer to the various components of the device used to collect sample, including conduits, tubes, void volumes, containers, walls and the like.

"Thermal contact" refers to a connection between components where there is heat flow such that the temperature of one component influences the temperature of another component that is in thermal contact, but in a manner that maintains operability and functionality of each component. Accordingly, the components in thermal contact may or may not be in direct physical contact. For example, there may be components disposed between the components in thermal contact that act as thermal conduits. The thermal contact does not adversely impact functionality of any of the components.

"Disinfectant" refers to carbon dioxide ($CO_2$) in its gas-phase, its liquid-phase, and its supercritical phase ($scCO_2$) in embodiments where only $scCO_2$ is dispersed into the area to be decontaminated. "Disinfectant" also includes a disinfectant additive in embodiments of the technology where both $scCO_2$ and the disinfectant additive are dispersed into the area to be decontaminated.

The devices described herein have a number of advantages over conventional collection devices. First, the device is effectively a "two-in-one" device that is compatible for collection of both liquid-phase samples and gas-phase samples. Second, the device can be used safely directly with a patient, to collect a liquid sample that corresponds to saliva (e.g., oral fluid (OF)) and a sample that is exhaled breath (EB) containing volatile organic compounds, semi-volatile compounds, proteins, lipids, polynucleotides and microbiota, such as bacteria and virus. Whether to collect an OF and/or an EB will depend in part, on the constituent of interest. In this manner, the collected specimen may be used for clinical infectious diseases, with the collection optionally performed by the to-be-tested individual without a need for active intervention by a trained caregiver. Third, the devices can maintain sample viability in a safely stored configuration that is transport ready, where viability is maintained even for relatively long time periods by a temperature-controlled container reservoir. As explained in the examples, the devices can operate at ambient pressure, or at a negative pressure. The negative pressure is particularly relevant in further reducing risk of inadvertent release of a hazardous agent to the external environment. The devices are particularly useful for one or more of: biomarker analysis from saliva, sputum, plasma, blood, urine, amniotic fluid, bone marrow, breast milk, synovial fluid, semen, vaginal fluid, mucus, or lymph; exhaled breath biomarker analysis; mucous dehydration markers; dehydration analysis; microbiota analysis; respiratory infection markers analysis; environmental exposure; collection of viruses, bacteria, fungus, and or polynucleotide sequences for use in a diagnostic assay.

Each of the devices described in Examples 1 through 3 herein may have some of the same or substantially similar components configured to safely store and transport biological samples such as bio-liquid (e.g. Oral fluid—OF), and/or gas phase (e.g. exhaled breath—EB) specimen collection for clinical infectious diseases for safe transportation and pre-processing for advanced analytical tests. For example, each of the devices described herein comprise a container 101, as shown in FIG. 1A (and also FIG. 2, FIG. 3A, and FIG. 3B) which generally, has a side wall 140, a bottom wall 141 and a top wall 142 to define a container reservoir 102. For a cylindrical container, there may be one curved side wall. Of course, other shapes are possible, including 3-sided, 4-sided, 5-sided, or more, side walls, including more box-like geometries or other geometries conducive with the particular application, including shipment of devices to testing facilities. In embodiments, the walls 140, 141, 142 of the container 101 may be insulated to reduce the transfer of heat from the container reservoir 102 to the external environment and/or reduce the transfer of heat from the external environment into the container reservoir 102. In further aspects of the technology, the walls 140, 141, 142 of the container 101 may include a shock-absorption layer made from natural rubber, silicone, neoprene, or a combination thereof. In some embodiments, the walls 140, 141, 142, of the container 101 may comprise one or more windows that are configured to permit the user to visually inspect any sensors or monitoring elements as well as spills or potential contamination in the device. For example, a colorimetric sensor may be used with a color change in the sensor indicating an out-of-range reading so that action may be taken to disinfect the device.

In each of the devices described in Examples 1 through 3, an inlet into the container reservoir 102 may correspond to a fluid port 104 having one or more openings (for example, a gas-phase opening 106 and/or a liquid-phase opening 158) wherein the fluid port 104 traverses the container 101 side wall 140 and extends between the container reservoir 102 and an external environment surrounding the device. In other words, the fluid port 104 provides fluidic connection from the external environment, such as where an individual introduces fluid to the port 104, and the container interior, where samples are collected and safely stored for transport, including with containers 120, 126. In some aspects of the technology, the fluid port 104 may be a hollowed L-shape or hollowed reverse L-shape defining a volume as illustrated in FIGS. 1A, 2, 3A, and 3B. The fluid port 104 fluidically connects a liquid biological sample inlet 108, and a gas biological sample inlet 110 to the container reservoir 102. In this manner, a user may insert a biological sample from the one or more openings of the fluid port 104, through the liquid biological sample inlet 108 and/or the gas biological sample inlet 110, into the container reservoir 102. In embodiments, the liquid biological sample inlet 108 and the gas biological sample inlet 110 are configured to receive OF and/or EB from a patient to be tested for a symptom of an infectious agent, including biomarkers and other analytes of the infectious agent. Of course, the liquid biological sample inlet 108 and the gas biological sample inlet 110 are also configured to receive other biological samples, such as blood or urine, as desired.

In some aspects of the technology, the one or more openings of the fluid port 104 may comprise the gas-phase opening 106. While it is referred to as the gas-phase opening 106, the gas-phase opening 106 may receive liquid, gas, and other fluid samples depending on the application of interest. For example, the gas-phase opening 106 may be configured to function as a mouthpiece, as illustrated in FIGS. 1A, 2, 3A, and 3B, wherein the mouthpiece may receive OF/EB directly from the mouth of an individual user. In other aspects of the technology, the one or more openings may be configured to receive an OF/EB injection from a syringe or another tool capable of injecting a biological sample. The OF may be a passive drool collection and the EB may be an exhaled breath condensate collection.

As shown in FIG. 1A (and also FIGS. 2, 3A, and 3B), each of the devices described in Examples 1-3 may also comprise a condensing spiral tube 122 having a spiral tube proximal end that is fluidically connected to the gas biological sample inlet 110 and a spiral tube distal end that is fluidically connected to a condensation sample container 126. In this manner, the connections are described as "fluidically connected" to describe the ability of a fluid, such as EB and/or OF, to flow from one component to another.

The condensing spiral tube 122 collects a gas-phase biological sample introduced to the gas biological sample inlet 110 via the one or more openings of the fluid port 104. The condensing spiral tube 122 is configured to convert the gas-phase biological sample, such as EB, to a condensed liquid sample 127 for collection by the condensation sample container 126. In embodiments, the condensing spiral tube 122 is comprised of tight spirals to provide a lengthened vapor path for the gas-phase biological sample to condense to the condensed liquid sample 127. In some aspects of the technology, the condensing spiral tube 122 may be constructed from glass, fiberglass, or a suitable polymer or metal. Each of the devices described herein is capable of receiving up to and including 100 mL of gas-phase biological sample. In examples, the user may exhale directly into the one or more openings of the fluid port 104 over an 8 to 12 minute collection time, with typical rates of about 80 μL to 120 μL of condensate per minute. The condensing spiral tube 122 is configured to condense at least a portion of the introduced gas-phase biological sample to the condensed liquid sample 127. In examples, the condensing spiral tube 122 may produce a maximum of 3 mL of condensed liquid sample 127 from the gas-phase biological sample.

In some embodiments, the condensation sample container 126 is configured to maintain the viability of biological samples, including infectious agents. Of course, each of the devices described in Examples 1-3 may be configured to have more than one of the condensation sample containers as illustrated in FIGS. 1A, 2, 3A, and 3B. This is especially useful where the biological samples will be tested by multiple laboratories and/or tested for multiple analytes of interest. The condensation sample container 126 may be a sample tube defining a container volume capable of storing a condensed liquid volume of less than or equal to 3 mL. For example, the condensation sample container 126 may be a microcentrifuge tube or other test tube with a cap. In embodiments, the condensation sample container 126 is sterilized before the collection of the condensed liquid sample 127. In further embodiments, the condensation sample container 126 has low binding properties to avoid the absorption of proteins, lipids, nucleotides, microbiota, and other analytes of interest. In embodiments, the condensation sample container 126 may be configured to detach from the condensing spiral tube 122 so that the user may remove the condensation sample container 126 from the device for analytical testing. In some aspects of the technology, the condensation sample container 126 may be configured to receive a stabilizer before the introduction of a sample in order to maintain the viability of the biological sample for testing. The collection containers 120 and 126 may be provided under a negative pressure to further facilitate sample collection and decrease risk of sample leakage out of the containers 120, 126. For example, sterile tubes with rubber stoppers (e.g., Vacutainer® specimen tubes).

The devices described in Examples 1-3 also comprise a tube 118 positioned within the container reservoir 102 having a tube proximal end that is fluidically connected to the liquid biological sample inlet 108 and a tube distal end that is fluidically connected to a liquid sample container 120. These connections are also described as "fluidically connected" to describe the ability of a fluid, such as OF, to flow from one component to another. In some embodiments, the tube 118 may be made from polymer such as polytetrafluoroethylene (PTFE or Teflon®), perfluoroalkoxy (PFA), or other materials that have similar coefficients of friction and similar electrical and thermal insulation properties. In other embodiments, the tube 118 may be made from glass or fiberglass. In further embodiments, the tube 118 has low binding properties to avoid the absorption of proteins, lipids, nucleotides, microbiota, or other analytes of interest. In aspects of the technology, the tube 118 is flexible. In other aspects of the technology, the tube 118 may be rigid with a longitudinal axis. In embodiments, there may be more than one tube 118 as illustrated in FIGS. 1A, 2, 3A, and 3B.

In some embodiments, the liquid sample container 120 is configured to maintain the viability of biological samples, including infectious agents. Of course, each of the devices described in Examples 1-3 may be configured to have more than one of the liquid sample containers as illustrated in FIGS. 1A, 2, 3A, and 3B. This is especially useful where the biological samples will be tested by multiple laboratories and/or tested for multiple analytes of interest. The liquid sample container 120 may be a sample tube defining a container volume to accommodate a liquid sample volume up to and including 3 mL. For example, the liquid sample container 120 may be a microcentrifuge tube or other test tube with a cap. In embodiments, the liquid sample container 120 is sterilized before the collection of the liquid sample. In further embodiments, the liquid sample container 120 has low binding properties to avoid the absorption of proteins, lipids, nucleotides, microbiota, or other analytes of interest. In embodiments, the liquid sample container 120 may be configured to detach from the tube 118 so that the user may remove the liquid sample container 120 from the device for analytical testing. In some aspects of the technology, the liquid sample container 120 may be configured to receive a stabilizer before the introduction of a sample in order to maintain the viability of the biological sample for testing.

Optionally, in some embodiments, there may be a filtration system 116 positioned between the tube 118 and the liquid biological sample inlet 108 configured to purify a liquid-phase biological sample 121 by removing debris before collection as specifically illustrated in FIG. 1A (and also FIGS. 1B, 2, 3A, and 3B). In embodiments, the filtration system 116 may be a nanofiltration device configured to include a filter membrane with a pore size range of 0.1 nm to 10 nm. In other embodiments, the filtration system 116 may be a microfiltration device configured to include a filter membrane with a pore size range of 0.1 μm to 10 μm. In another embodiment, the filtration system 116 may be an ultrafiltration device. The pore size range may be optimized to facilitate purified biological sample collection based on the analyte of interest. For example, the remote testing facility may require that the liquid-phase biological sample 121 be free from bacteria, so the microfiltration device may be optimal. Additionally, a material of the filter membrane may be optimized to facilitate purified biological sample collection based on the analyte of interest.

Figure 1B:
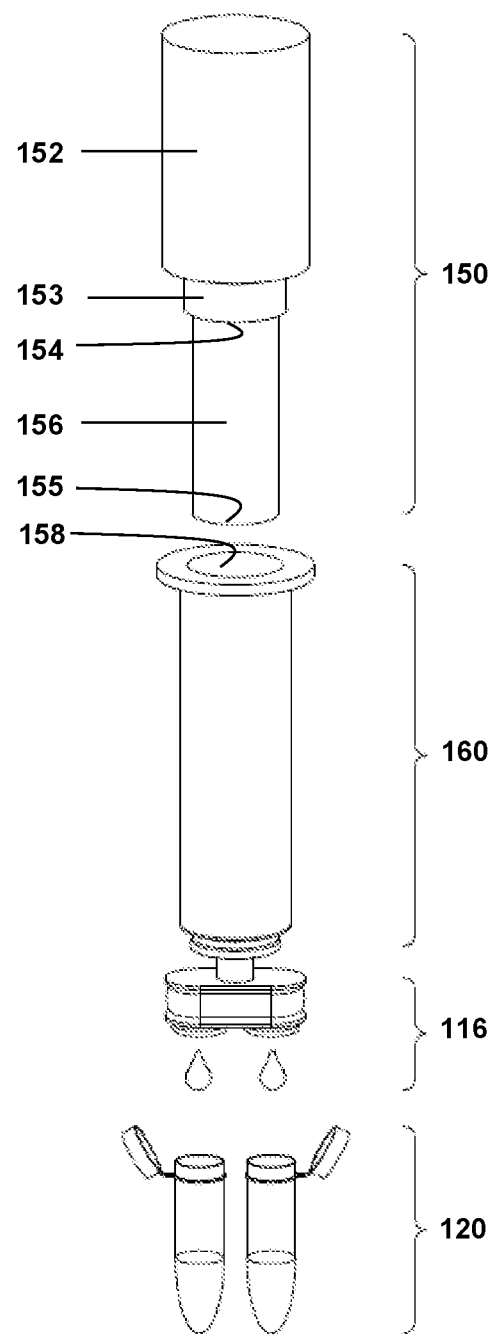
FIG. 1B illustrates an exemplary insertable biofluid collector configured for insertion into an insert port of a portable containment device, including as illustrated in FIG. 1A.
Figure 2:
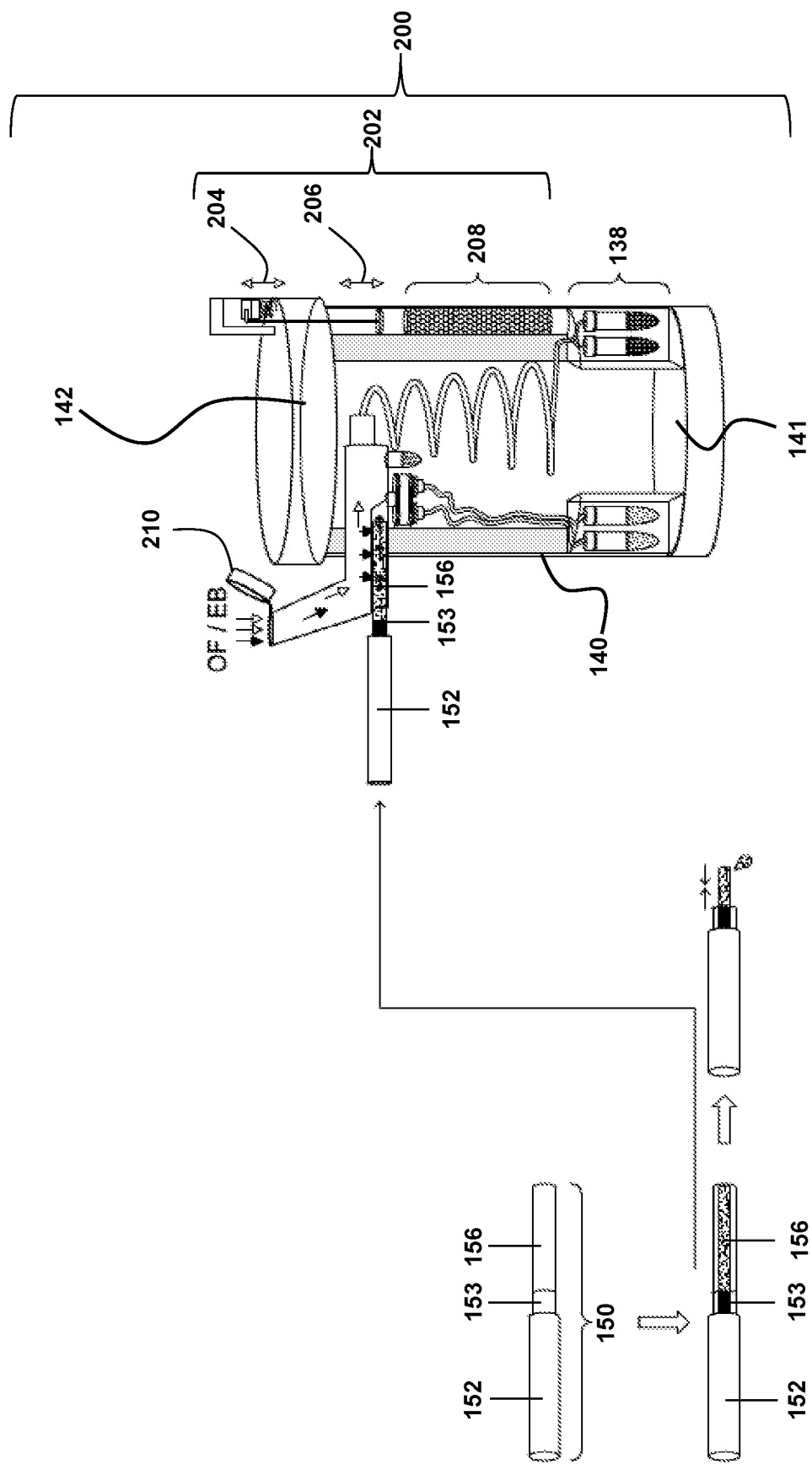
FIG. 2 illustrates portable biocontainment direct-access device for collecting, storing and transporting a hazardous or an infectious agent. The device is a two-in-one disposable device design configured for operation under negative pressure containment (NPC).

In some embodiments, an excess liquid collection container 114 may be fluidically connected to the fluid port 104 as illustrated in FIGS. 1A, 2, 3A, and 3B for preventing excess liquid from entering the liquid biological sample inlet 108 to collection container(s) 120. In aspects of the technology, the excess liquid collection container 114 may be constructed from polypropylene. The excess volume that may be encountered dictates the volume of the excess liquid collection container 114. Typical volumes may correspond to up to and including 5 mL. Of course, in embodiments, there may be more than one excess liquid collection container 114. The excess liquid collection container 114 is configured to receive excess liquid entering the device from the one or more openings of the fluid port 104 such as the gas-phase opening 106 as illustrated in FIG. 1A and/or the liquid-phase opening 158 as illustrated in FIGS. 1B and 2. In this manner, there is a built-in fail safe to avoid overfilling of liquid sample container(s) 120.

As shown in FIG. 1A, the devices described in Examples 1-3 may optionally include a cooling chamber 130 positioned in the container reservoir 102 configured to receive a cooling element 128. In aspects of the technology, the cooling chamber 130 may be in thermal contact with the condensing spiral tube 122. In further aspects of the technology, the cooling chamber 130 may be in thermal contact with other components, such as "collection components" like the condensation sample container 126 and the liquid sample container 120. In this manner, both sample preservation and condensation of the gas-phase biological sample (e.g., EB) is facilitated by the cooling element 128. In some embodiments, the cooling element 128 may be ice, jelly ice, dry ice, or a similar cooling element capable of cooling the condensing spiral tube 122, the condensation sample container 126, and/or the liquid sample container 120. In aspects of the technology, the cooling chamber 130 may be at least one cooling jacket configured to wrap around the condensing spiral tube 122. In further embodiments, the at least one cooling jacket may be configured to wrap around the condensation sample container 126 and the liquid sample container 120. In other aspects of the technology, the cooling chamber 130 may be a compartment having at least one side wall, a bottom wall, and a detachable lid defining a cooling chamber volume wherein the cooling chamber 130 is in thermal contact with the condensation sample container 126, the liquid sample container 120, and the condensing spiral tube 122.

In aspects of the technology, the top wall 142 of the container 101 is a removable cap 112, which may be configured to detach to allow for the insertion of the cooling element 128 and reattach once the cooling element 128 is inserted. In some embodiments, the removable cap 112 is configured to twist on and off of the side walls 140 of the container 101, such as a threaded screw closure. In other embodiments, the removable cap 112 is a friction fit, such that the removable cap 112 may be removed and attached with the use of force. In some aspects of the technology, the removable cap 112 may be sealed with a vacuum. In some embodiments, the removable cap 112 may be configured to accept a plurality of fasteners, such as screws or nails that are configured to attach to the side walls 140 of the container 101. In further aspects of the technology, the removable cap 112 may be configured to lock to the container 101. The removable cap 112 may be used with any of the devices described in Examples 1-3.

Figure 3A:
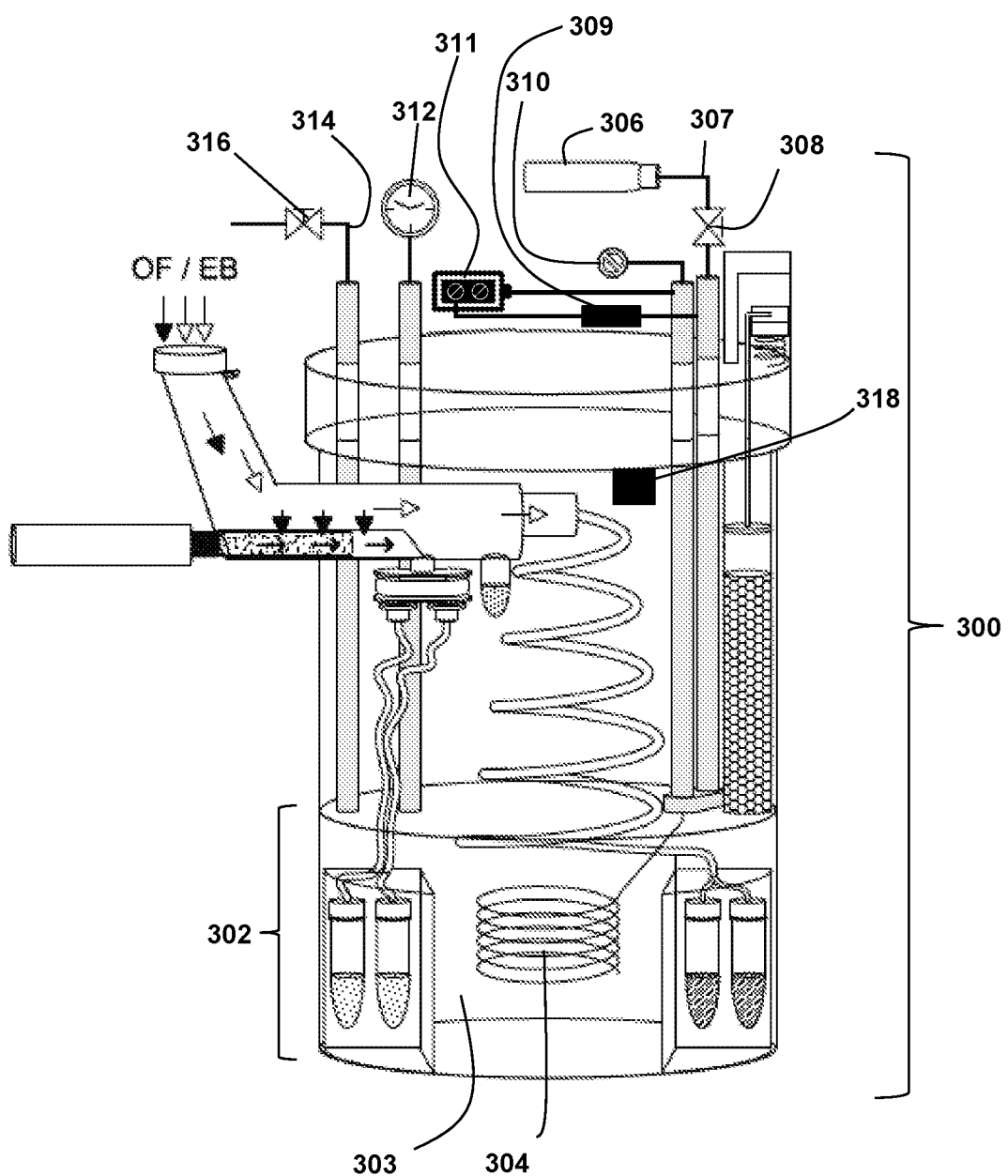
FIG. 3A illustrates a portable biocontainment device, such as a two-in-one decontamination disposable device, configured to include a targeted release of $scCO_2$ into a compartment within the two-in-one disposable device.
Figure 3B:
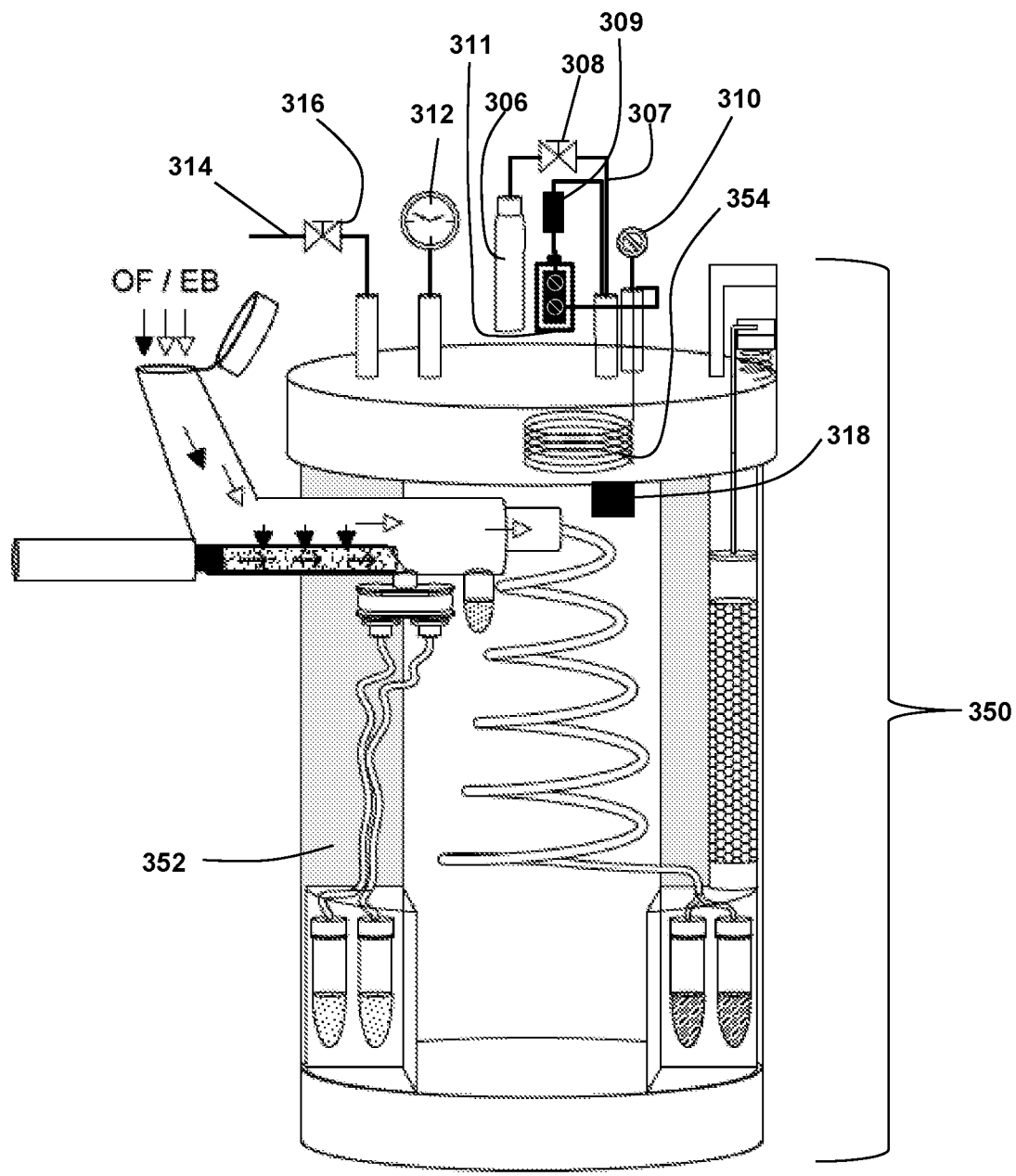
FIG. 3B illustrates a device configured to include a non-targeted release of $scCO_2$.

In some embodiments, there is an optional cover that is configured to attach to the top wall 142 of the container 101 to protect any components of the device that at least partially protrude from the container 101, such as those illustrated in FIGS. 2, 3A, and 3B. The optional cover may be constructed from polymer, metal, fiberglass, or any other rigid and durable material. In this manner, any components of the device that at least partially protrude from the container 101 are protected from disturbances, such as rough handling by carriers during shipment of the device. In embodiments, the attachment to the top wall 142 of the container 101 may be facilitated by a threaded screw closure, friction fit, or vacuum seal.

As illustrated in FIG. 1A (and also FIGS. 2, 3A, and 3B), a liquid sample collection outlet 136 and a condensation sample collection outlet 138 may be positioned within the container reservoir 102 to provide access to the liquid sample container 120 and the condensation sample container 126 by the user from the external environment. Each sample collection outlet 136, 138 may have at least two walls to define a sample collection outlet volume. In aspects of the technology, the liquid sample container 120 may be positioned within the sample collection outlet volume of the liquid sample collection outlet 136, and the condensation sample container 126 may be positioned within the sample collection outlet volume of the condensation sample collection outlet 138. In embodiments, the sample collection outlet volume of the liquid sample collection outlet 136 is large enough to house at least two of the liquid sample containers 120. Similarly, in embodiments, the sample collection outlet volume of the condensation sample collection outlet 138 is large enough to house at least two of the condensation sample containers 126. In some aspects of the technology, each of the sample collection outlets, 136, 138, is configured to reduce the movement of, as well as shock applied to, the sample containers 120, 126 to facilitate safe transportation of the biological samples. For example, each of the sample collection outlets 136, 138, may comprise a padding that is molded to cushion the sample containers 120, 126. The padding may be made from foam, paper, polymer, air pillows, cellulose, textiles, or any combination thereof. In some embodiments, each sample collection outlet 136, 138 may have a sealable door operably connected to the side wall 140 or bottom wall 141 of the container 101. In this manner, each sample collection outlet 136, 138 may be configured to open to the external environment to allow a user to access the sample container(s) 120, 126. In aspects of the technology, the sealable door may be a sliding door. In other aspects of the technology, the sealable door may be a hinged door.

In some embodiments, each of devices described in Examples 1-3 may be used to collect samples that are used for any one or more of: biomarker analysis from a biological fluid sample, including saliva, sputum, plasma, blood, urine, amniotic fluid, bone marrow, breast milk, synovial fluid, semen, vaginal fluid, mucus, or lymph; exhaled breath biomarker analysis; noninvasive based dehydration marker analysis; microbiota analysis; dehydration analysis; respiratory infection markers analysis; environmental exposure to a chemical, biological, radiological, nuclear and/or explosive (CBRNE) agent; and/or a diagnostic assay at a remote facility for detecting one or more of a virus, bacteria, fungus and/or a polynucleotide sequence (e.g., DNA and/or RNA). Analysis of the biological fluid sample may include determination of the presence or absence of the analytes of interest as well as specific sequences thereof.

Example 1: Ambient Pressure Operation

FIG. 1A illustrates an ambient pressure two-in-one device 100 configured to safely collect, store, and transport biological samples in ambient pressure.

In an embodiment, the ambient pressure two-in-one device 100 comprises the container 101, as shown in FIG. 1A (and also FIG. 2, FIG. 3A, and FIG. 3B). In embodiments, the walls 140, 141, 142 of the container 101 may be constructed from polymer, glass, fiberglass, metal or other material capable of safely storing and transporting the biological samples in various environmental conditions, such as moisture, altitude up to 43,000 feet, UV light, shock force, and temperatures ranging from about −60° C. to about 60° C. The ambient pressure two-in-one device 100 may also accommodate transport times of up to 28 hours.

In some embodiments, the fluid port 104 may be constructed from the same or substantially similar material as the container 101. In aspects of the technology, the one or more openings of the fluid port 104 may be a single opening, such as the gas-phase opening 106, configured to receive both the liquid-phase biological sample 121 and the gas-phase biological sample. The reception of both the liquid-phase biological sample 121 and the gas-phase biological sample may occur contemporaneously, in tandem. The one or more openings of the fluid port 104 may also be configured to receive either liquid-phase biological samples 121 or gas-phase biological samples.

To facilitate safe transportation, in some aspects of the technology, the ambient pressure two-in-one device 100 may further comprise a fail-safe filter 132 positioned within the walls 140, 141, 142 of the container 101. In this position, the fail-safe filter 132 may prevent the release of infectious agents and/or biohazardous material into the external environment if the walls 140, 141, 142 of container 101 crack or leak in some other manner. In some embodiments, the fail-safe filter 132 may be a carbon block. In other embodiments, the fail-safe filter 132 may be a Kappa® Filter or a similar filter from the same or different manufacturer employing similar air pollution and contamination reduction technology. The fail-safe filter 132 may be used with any of the devices described herein.

FIG. 1B illustrates an insertable liquid collector 150 for optional use with any of the devices described herein, including as specifically illustrated in FIG. 2 (and also FIGS. 1A, 3A, and 3B). In embodiments, the insertable liquid collector 150 may have a hand bar 152, a compressible absorbent pad 156, and a liquid indicator 153. The compressible absorbent pad 156 has an absorbent pad first end 155 and an absorbent pad second end 154. In some embodiments, the hand bar 152 may be connected to the absorbent pad second end 154 and/or the liquid indicator 153. For example, the hand bar 152 connects to both the absorbent pad second end 154 and the liquid indicator 153 in embodiments where the liquid indicator 153 at least partially extends from the absorbent pad second end 154 to the absorbent pad first end 155. In other examples, the hand bar 152 connects to the liquid indicator 153, and not directly to the absorbent pad second end 154 in embodiments where the liquid indicator 153 is positioned in between the hand bar 152 and the compressible absorbent pad 156 as illustrated in FIG. 1B. The hand bar 152 may be constructed from polymer and is configured to be held by an operator for handling the insertable liquid collector 150.

The insertable liquid collector 150 may be inserted into the one or more openings of the fluid port 104 to transfer the liquid-phase biological sample into the container reservoir 102. In preferred embodiments, the one or more openings of the fluid port 104 comprise the gas-phase opening 106 and a liquid-phase opening 158. In this manner, gas-phase biological samples enter the device through the gas-phase opening 106 and liquid-phase biological samples 121 enter the device through the liquid-phase opening 158. To facilitate the entrance of the liquid-phase biological samples 121 into the device, the fluid port 104 is configured to house an insert port 160 that extends between the liquid-phase opening 158 and the liquid biological sample inlet 108, wherein the insert port 160 is configured to receive the insertable liquid collector 150. The insert port 160 is fluidically connected to the liquid biological sample inlet 108. In this manner, the insertable liquid collector 150 may transport the liquid-phase biological samples 121 from the compressible absorbent pad 156 to the liquid biological sample inlet 108.

The compressible absorbent pad 156 is configured to absorb the liquid-phase biological sample 121. In one example, the user may dip the absorbent pad first end 155 into a vessel containing the liquid-phase biological sample 121. In other examples, the user may insert the absorbent pad first end 155 into the user's mouth to absorb the liquid-phase biological sample 121. In further examples, the user may place the compressible absorbent pad 156 under a stream of urine to collect a urine sample. Of course, the methods of liquid-phase biological sample 121 collection with the insertable liquid collector 150 are not limited to the described examples as there are many various ways that an absorbent material may absorb a liquid-phase sample. To facilitate absorption, in some embodiments, the compressible absorbent pad 156 may be made from nonwoven fibers, such as rayon polyester blends, 100% cotton, such as Ahlstrom-Munksjo Grade 320 or Whatman™ Schleicher & Schuell Grade 603, nanocellulose substrate, other highly absorbent material, or any combination thereof.

In other aspects of the technology, the liquid indicator 153 may be aligned with the longitudinal axis of the compressible absorbent pad 156 and may be configured to change color, from white to red for example, when the compressible absorbent pad 156 reaches a predetermined saturation threshold. In this manner, the user is alerted to insert the insertable liquid collector 150 into the insert port 160. The predetermined saturation threshold may be established when the liquid-phase biological sample 121 travels along the compressible absorbent pad 156 through capillary action and reaches the liquid indicator 153 thereby causing the liquid indicator 153 to change color. In some embodiments, the changed color may be facilitated by the presence of liquid-sensitive dyes embedded within the liquid indicator 153.

In preferred embodiments, the insert port 160 has two openings, the liquid-phase opening 158 and the liquid biological sample inlet 108. In this manner, the compressible absorbent pad 156 may be compressed within the insert port 160 to transfer the liquid-phase biological sample 121 from the compressible absorbent pad 156 into the liquid biological sample inlet 108. To facilitate the transfer of the liquid-phase biological sample 121 from the compressible absorbent pad 156 into the liquid biological sample inlet 108, the compressible absorbent pad 156 may be compressed by the user inserting the insertable liquid collector 150 into the insert port 160 until the insertable liquid collector 150 is fully inserted. In this manner, upon the compression of the compressible absorbent pad 156, the liquid-phase biological sample 121 is forced out of the compressible absorbent pad 156, through the liquid biological sample inlet 108, and into the tube 118 for transport to the liquid sample container 120. Of course, as illustrated by dark arrows, the liquid may also flow from an individual spitting into the gas-phase opening 106 and, via apertures 170, onto absorbent pad 156 that is positioned into the insert port 160.

In some embodiments, the hand bar 152 protrudes from the insert port 160 to allow for the user to control the compression of the absorbent pad 156. In further aspects of the technology, the hand bar 152 may be configured to lock into the insert port 160 to provide continued compression of absorbent pad 156 as illustrated in FIG. 2. For example, one end of the hand bar 152 may have an external thread capable of mating with an internal thread of the insert port 160 wherein the user may twist the hand bar 152 to lock it into the insert port 160 once the insertable fluid collector 150 is fully inserted. In embodiments, this locking mechanism is capable of creating a leak-proof seal configured to prevent the escape of liquid and/or air. In further aspects of the technology, the locking mechanism may create a permanent seal, including by tabs and recess features in combination with a tight-fit, and/or gaskets.

In other embodiments, a device that comprises the components for the insertable liquid collector 150 may still receive liquid-phase biological samples 121 from the gas-phase opening 106 of the fluid port 104. In such embodiments, the liquid-phase opening 158 may be sealed with a plug and the insert port 160 may have a plurality of apertures 170 at its dorsal side configured to receive the liquid-phase biological sample 121 collected through the gas-phase opening 106 as reflected by the dark arrows in FIG. 1A (and also FIGS. 2, 3A, and 3B). In this manner, the user may expel both liquid-phase biological samples 121 and gas-phase biological samples directly to the gas-phase opening 106 of the fluid port 104 even where the fluid port 104 is configured to house the insert port 160. Without the plurality of apertures 170 on the insert port 160, the liquid-phase biological sample 121 could not flow from the gas-phase opening 106 into the liquid biological sample inlet 108. Optionally, in these embodiments, the insert port 160 may be configured to receive a removable liquid collection conduit 175 to seal the plurality of apertures 170 of the insert port 160. The removable liquid collection conduit 175 extending from the liquid-phase opening 158 to the liquid biological sample inlet 108. In this manner, the compressible absorbent pad 156 may be compressed in the insert port 160 without the liquid-phase biological sample 121 escaping through the plurality of apertures 170 of the insert port 160.

Example 2: Negative Pressure Containment (NPC)

To further facilitate safety, the device may operate under a negative pressure relative to atmosphere. In this manner, leaks out of the containment chamber to the external environment is further minimized.

FIG. 2 illustrates a NPC embodiment 200. To generate NPC, a pressure pump assembly 202, comprising a spring 204, a vent 206, and a filter 208, is operably connected to the container reservoir 102. The spring 204 is configured to remove air from the container reservoir 102 to create a negative pressure. In embodiments, the spring 204 may at least partially protrude from the removable cap 112 as shown in FIG. 2 in order to facilitate the flow of air from the container reservoir 102 to the external environment. In such embodiments, the removable cap 112 is configured to detach from the container 101 without damaging the pressure pump assembly 202. In other embodiments, the spring 204 may not protrude from the removable cap 112 and is embedded within the walls 140, 141, 142 of the container 101. In some embodiments, the spring 204 may be manually engaged by the user. In other embodiments, the spring 204 may be automated to facilitate the flow of air. The vent 206 is configured to open to the external environment while the spring 204 removes air from the container reservoir 102. In contrast, the vent 206 is configured to close to maintain the negative pressure in the container reservoir 102 after the spring 204 creates the negative pressure. The filter 208 may be positioned between the container reservoir 102 and the vent 206. In embodiments, the filter 208 is configured to capture biological agents, biocontaminants, and non-biological agents and contaminants from entering the external environment. In aspects of the technology, the filter 208 may be made from the same or substantially similar material as the fail-safe filter 132 described in Example 1.

To maintain the NPC, the container 101 may be configured to withstand negative pressure. For example, the walls 140, 141, 142 of the container 101 may be constructed from a rigid, airtight material. In embodiments, the walls 140, 141, 142 of the container 101 may be constructed from polymer, glass, fiberglass, or other material capable of safely storing and transporting the biological samples in various environmental conditions, such as moisture, UV light, and shock force, and temperatures ranging from about −60° C. to about 60° C. The NPC embodiment 200 may also accommodate transport times of up to 28 hours.

To further maintain the NPC, the one or more openings of the fluid port 104 may comprise one or more closers 210 that seal the fluid port 104 from the external environment after collection. In embodiments, the one or more closers 210 may be configured to prevent liquid and/or air from entering into and leaving from the device by creating an airtight seal with the fluid port 104. In some aspects of the technology, the one or more closers 210 may be an attachable lid as illustrated in FIG. 2. In other aspects of the technology, the one or more closers 210 may be a screw cap, a plug, or other closure capable of sealing the fluid port 104 from the external environment. In some embodiments, the one or more closers 210 may irreversibly attach to the fluid port 104. Additionally, in embodiments, the hand bar 152 of the insertable liquid collector 150 is configured to create an airtight seal with the insert port 160 to maintain the NPC. As desired, the fluid port 104 may be removable, and the closer 210 configured to seal the orifice that accommodates the fluid port 104 through the side wall 140 of the container 101.

Example 3: Supercritical Carbon Dioxide ($scCO_2$) Safety Feature

Example 3 describes embodiments of the portable biocontainment device that are capable of decontaminating the device with supercritical carbon dioxide ($scCO_2$) or $scCO_2$ and a disinfectant additive. The disinfectant additive is beneficial for the sterilization process as $scCO_2$ may not reliably decontaminate some contagious samples alone, such as bacterial endospores. However, $scCO_2$ is still effective as a disinfectant on its own for many contagious samples. Therefore, each of the devices described in Example 3 may be configured to decontaminate the device with either $scCO_2$ alone, or $scCO_2$ and the disinfectant additive. Bennet et al., *Evaluation of Supercritical $CO_2$ Sterilization Efficacy for Sanitizing Personal Protective Equipment from the Coronavirus SARS-CoV-2*, Elsevier, 18 Mar. 2021; Bernhardt et al., *Improved Sterilization of Sensitive Biomaterials with Supercritical Carbon Dioxide at Low Temperature*, PLOS One, Jun. 12, 2015.

In embodiments, the disinfectant additive may be a liquid solution comprising peroxides, peracetic acid-based co-solvents, carboxylic acids, alcohols, and mixtures thereof. In other embodiments, the disinfectant additive may be a dehydrated liquid solution in the form of a dissolvable tablet. In further embodiments, the disinfectant additive may be a dehydrated liquid solution dried on a membrane or other suitable carrier. In any of the disinfectant compositions, the disinfectant additive may comprise more than or equal to 300 mg/L of hydrogen peroxide. In other examples, the disinfectant additive may comprise about 75% ethanol with about 15% hydrogen peroxide or peracetic acid-based co-solvents and about 10% water. In further examples, the disinfectant additive may comprise about 5% peracetic acid, about 22% hydrogen peroxide, about 10% acetic acid, and about 63% water. In embodiments, 2 mL to 7 mL of either the liquid solution disinfectant additive or the rehydrated disinfectant additive may be added to the device wherein the area to be decontaminated has a volume of 600 mL.

FIG. 3A illustrates an embodiment of the devices described herein that is capable of a targeted dispersal of disinfectant to decrease the risk of biohazardous material from entering the external environment in the event of device failure. One benefit of a targeted disinfectant dispersal device 300 is that if a collected sample leaks from one of the sample containers 120, 126 the leak is contained within a confined area even if the fluid port 104 of the container 101 is dislodged or the removable cap 112 breaks from the container 101. In embodiments, the walls 140, 141, 142 of the container 101 of the targeted disinfectant dispersal device 300 may be constructed from metal, polymer, glass, fiberglass, or other material capable of safely storing and transporting the biological samples in various environmental conditions, such as moisture, altitudes up to 43,000 feet, UV light, and shock force, and temperatures ranging from about −60° C. to about 60° C. The targeted disinfectant dispersal device 300 may also accommodate transport times of up to 28 hours.

The targeted disinfectant dispersal device 300 is configured to limit the dispersal of disinfectant to a pressure vessel 302. The pressure vessel 302 comprising at least one airtight barrier separating the sample containers 120, 126 from the remainder of the container reservoir 102. For example, in some embodiments, the at least one airtight barrier may extend horizontally across the side walls 140 of the container 101 to create a pressure vessel volume 303 wherein the sample containers 120, 126 are positioned within said pressure vessel volume 303. In other embodiments, the at least one airtight barrier may be an enclosed, hollowed capsule creating a pressure vessel volume 303 wherein the sample containers 120, 126 are positioned within said pressure vessel volume 303.

The pressure vessel 302 is constructed to maintain pressure levels and temperature levels required to convert $CO_2$ to $scCO_2$. In embodiments, the pressure vessel 302 may maintain a pressure of up to 2500 psi and a temperature of up to 60° C. within the pressure vessel volume 303. The pressure vessel 302 may maintain such pressure range and temperature for a time period of between 10 to 60 minutes. For example, in some aspects of the technology the pressure vessel 302 may maintain a pressure range of 1500 psi to 2000 psi and a temperature range of 30° C. to 35° C. for a period of 20 to 40 minutes to sterilize the contents within the pressure vessel volume 303. In further aspects of the technology, the pressure vessel 302 is configured to withstand depressurization cycles and pressurization cycles for a period between 10 to 60 minutes. In some embodiments, the pressure vessel 302 may be constructed from steel, aluminum, or other metal capable of withstanding a pressure up to 2500 psi and a temperature of up to about 40° C. for up to 50 minutes.

A pressure sensor 312 may be operably attached to the container 101 and configured to monitor the pressure within the pressure vessel volume 303. In some embodiments, the pressure sensor 312 may be operably attached to the removable cap 112. In such embodiments, the removable cap 112 may be configured to attach to, and detach from, the container 101 without disrupting the operability of the pressure sensor 312. For example, the removable cap 112 may comprise an airtight tunnel wherein the pressure sensor 312 may extend through the airtight tunnel. In embodiments, the pressure sensor 312 may at least partially protrude from the container 101 wherein the user may visually inspect a reading on the pressure sensor 312. In other embodiments, the pressure sensor 312 may be positioned within the container reservoir 102 and the user may perform visual inspection through the one or more windows of the walls 140, 141, 142 of the container 101. The pressure sensor 312 may be a mechanical sensor and/or an electronic sensor. The pressure sensor 312 may have an analog display and/or a digital display.

Additionally, an exhaust line 314 may be operably attached to the container 101 having an exhaust line proximal end and an exhaust line distal end. The exhaust line proximal end is operably connected to the pressure vessel volume 303 and the exhaust line distal end opens to the external environment to facilitate the flow of exhaust from the pressure vessel volume 303 to the external environment. In some embodiments, the exhaust line 314 may be operably attached to the removable cap 112. In such embodiments, the removable cap 112 may be configured to attach to, and detach from, the container 101 without disrupting the operability of the exhaust line 314. For example, the removable cap 112 may comprise an airtight tunnel wherein the exhaust line 314 may extend through the airtight tunnel. In embodiments, an exhaust controller 316 is connected to the exhaust line 314. In embodiments, the exhaust controller 316 may be a manual controller such as a valve, a pump, a syringe pump, or the like that is at least partially positioned outside of the container 101 to allow the user to manually adjust the pressure within the pressure vessel 302. Preferably, the exhaust controller 316 is electronically controlled for automated flow of exhaust from the pressure vessel volume 303 to the external environment during a fail-safe event, such as a sudden pressure drop, a high impact force, a component breakage, etc., any of which may be monitored by one or more sensors 318.

The temperature within the pressure vessel volume 303 is controlled by a controllable heating element 304. In embodiments, the controllable heating element 304 may be positioned within the pressure vessel volume 303 as illustrated in FIG. 3A. In other embodiments, the controllable heating element 304 may be positioned along the border of the at least one airtight barrier of the pressure vessel 302. In embodiments, the controllable heating element 304 may be a heating coil made from metal, ceramic, or other material capable of heating the pressure vessel volume 303 up to at least 60° C.

The controllable heating element 304 is operably connected to an automatic controller 311. In embodiments, the automatic controller 311 is operably connected to the container 101 and is at least partially positioned outside of the container 101 to allow the user to visually inspect a temperature reading. In other embodiments, the automatic controller 311 may be positioned within the container reservoir 102 and the user may perform visual inspection through the one or more windows of the walls 140, 141, 142 of the container 101. The automatic controller 311 may comprise an analog thermometer and/or a digital temperature display. In some embodiments, the automatic controller 311 may be operably attached to the removable cap 112. In such embodiments, the removable cap 112 is configured to attach to, and detach from, the container 101 without disrupting the operability of the automatic controller 311. For example, the removable cap 112 may comprise an airtight tunnel wherein the automatic controller 311 may extend through the airtight tunnel. As its name suggests, the automatic controller 311 is an automated system wherein the system is preset to adjust the controllable heating element 304 once a predetermined external stimuli is recognized, such as a predetermined impact threshold or a component breakage, any of which may be monitored by the one or more sensors 318.

The controllable heating element 304 may also operably connect to a manual temperature controller 310. In embodiments, the manual temperature controller 310 is operably connected to the container 101 and is at least partially positioned outside of the container 101 to allow the user to manually adjust the controllable heating element 304. The manual temperature controller 310 may comprise a dial, a knob, a handle, digital buttons, a touch screen, or the like. The manual temperature controller 310 may further comprise an analog thermometer and/or a digital temperature display. In some embodiments, the manual temperature controller 310 may be operably attached to the removable cap 112. In such embodiments, the removable cap 112 is configured to attach to, and detach from, the container 101 without disrupting the operability of the manual temperature controller 310. In embodiments where the device comprises both the automatic controller 311 and the manual temperature controller 310, the user may adjust the temperature within the device in instances where the automatic controller 311 fails to adjust the temperature after the predetermined external stimuli is recognized.

The liquid sample container 120 and the condensation sample container 126 are positioned within the pressure vessel volume 303 as illustrated in FIG. 3A. In this manner, if a collected sample leaks from one of the sample containers 120, 126, the dispersal of disinfectant in the pressure vessel volume 303 may decontaminate the leak.

To facilitate the dispersal of $scCO_2$ or $scCO_2$ and the disinfectant additive into the pressure vessel volume 303, one or more storage containers 306 may be connected to the pressure vessel 302 via one or more disinfectant lines 307. The one or more storage containers 306 may be constructed from stainless steel, aluminum, polyurethane, carbon steel, or the like. In embodiments, the one or more storage containers 306 are insulated. In aspects of the technology, at least one of the one or more storage containers 306 is configured to store $CO_2$ in its gas-phase, its liquid-phase, or a mixture of both. In embodiments, at least one of the one or more storage containers 306 is configured to store the disinfectant additive. In preferred embodiments, the $CO_2$ and the disinfectant additive may be stored in the liquid phase.

The one or more disinfectant lines 307 have a disinfectant line proximal end and a disinfectant line distal end, wherein the one or more storage containers 306 are operably connected to the disinfectant line proximal end and the pressure vessel 302 is operably connected to the disinfectant line distal end. In embodiments, the one or more storage containers 306 are positioned outside of the container 101. In embodiments, the removable cap 112 is configured to attach to, and detach from, the container 101 without disrupting the operability of the one or more disinfectant lines 307. For example, the removable cap 112 may comprise an airtight tunnel wherein the one or more disinfectant lines 307 may extend through the airtight tunnel. In some aspects of the technology, the one or more disinfectant lines 307 is a tube made from polyvinyl chloride (PVC), silicone, or a similar material that is capable of allowing the transport of the $CO_2$ in its liquid phase, $scCO_2$, and the disinfectant additive.

In embodiments, the automatic controller 311 is operably connected to a disinfectant pump 309 as well as the controllable heating element 304 to control the flowrate of the $CO_2$ and the temperature of the controllable heating element 304. In further embodiments, the automatic controller 311 and the disinfectant pump 309 are also configured to control the flowrate of the disinfectant additive. The disinfectant pump 309 is positioned between the automatic controller 311 and the one or more disinfectant lines 307 and is operably connected to the one or more disinfectant lines 307. The automatic controller 311 is electronically controlled for automated flow of disinfectant during a fail-safe event which may be monitored by the one or more sensors 318. For example, the automatic controller 311 may be configured to receive a signal from the one or more sensors 318 when a predetermined impact threshold is reached. In response, the automatic controller 311 is configured to engage the disinfectant pump 309 to increase the flowrate of disinfectant through the one or more disinfectant lines 307 and into the pressure vessel volume 303. Additionally, the automatic controller 311 is configured to engage the controllable heating element 304 to increase its temperature to a temperature range suitable to transform the $CO_2$ to $scCO_2$. In this manner, the decontamination of device is possible. In embodiments, the automatic controller 311 may have a switch or a button that allows the user to manually engage the decontamination procedure with the automatic controller 311.

In some embodiments, the one or more disinfectant lines 307 are also operably connected to a manual disinfectant controller 308. The manual disinfectant controller 308 may be a valve, a knob, a handle, a touch screen, digital buttons, or the like, positioned outside of the container 101 to allow the user to manually control the flowrate of the $CO_2$ and the disinfectant additive. Other representative manual flow controllers include pumps, syringe pumps, or the like.

In preferred embodiments, the one or more sensors 318 are in wired or wireless communication with the exhaust controller 316 and the automatic controller 311. Wireless communication may include Bluetooth, infrared communication, radio frequencies, and the like. The one or more sensors 318 may be programmed to send a fail-safe signal to the exhaust controller 316 and the automatic controller 311 when a preprogrammed threshold is detected, such as a predetermined impact threshold, a predetermined change in pressure, a predetermined moisture threshold, etc. The exhaust controller 316 and the automatic controller 311 may be preprogrammed to respond to the fail-safe signal.

In some embodiments, the one or more sensors 318 may also be in wired or wireless communication with the pressure sensor 312 wherein the pressure sensor 312 receives and displays the fail-safe signal. Upon receiving the fail-safe signal, the pressure sensor 312 may indicate that the fail-safe signal has been received, such as by displaying a red X or "contamination possible." In this manner, if the $scCO_2$ and/or the disinfectant additive was not released automatically, and/or the controllable heating element 304 did not increase its temperature, the user may visually inspect the container reservoir 102 and manually engage the manual disinfectant controller 308 and/or the manual temperature controller 310. Of course, the user may also visually inspect the container reservoir 102 and manually engage the manual controllers 308, 310 without the pressure sensor 312 display. In some embodiments, the automatic controller 311 may also be configured to display a warning upon receiving the fail-safe signal from the one or more sensors 318.

FIG. 3B illustrates an embodiment of the devices described herein that is capable of a non-targeted dispersal of disinfectant to decrease the risk of biohazardous material from entering the external environment in the event of device failure. One benefit of the non-targeted disinfectant dispersal device 350 is that if there is a leak anywhere within the container reservoir 102 (ex: if there is a micro tear in the tube 118) the leak will be decontaminated.

The non-targeted disinfectant dispersal device 350 is configured to release disinfectant into the container reservoir 102 in the event of device failure. The container 101 is constructed from pressure containment walls 352 configured to contain pressure levels and temperature levels required to transform $CO_2$ to $scCO_2$. In further aspects of the technology, the pressure containment walls 352 are configured to withstand depressurization cycles and pressurization cycles for a period between 10 to 60 minutes. In preferred embodiments, the pressure containment walls 352 are constructed from stainless steel. In other embodiments, the pressure containment walls 352 may be constructed from glass, fiberglass, plastic, aluminum, carbon steel, or other material capable of containing pressure and temperature levels required to transform the $CO_2$ to $scCO_2$. In embodiments, with these pressure containment walls 352 the container reservoir 102 may maintain a pressure up to 2500 psi and a temperature of up to about 60° C. The pressure containment walls 352 may maintain such pressure range and temperature for a time period of between 10 to 60 minutes. For example, the pressure containment walls 352 may maintain a pressure range of 1500 psi to 2000 psi and a temperature range of 30° C. to 35° C. for a period of 20 to 40 minutes to sterilize the container reservoir 102. Similar to the targeted disinfectant dispersal device 300, the pressure sensor 312 may be attached to the container 101 and may be configured to monitor the pressure within the container reservoir 102. The exhaust line 314 extends between the container reservoir 102 and the external environment.

To facilitate the disinfectant dispersal, the one or more storage containers 306 are connected to the container reservoir 102 via the one or more disinfectant lines 307, wherein the disinfectant line distal end opens to the container reservoir 102. In embodiments, the one or more disinfectant lines 307 at least partially traverse a controllable preheating element 354. In this manner, the $CO_2$ flows through the controllable preheating element 354 via the one or more disinfectant lines 307 before reaching the container reservoir 102 which has been pressurized to transform the $CO_2$ to $scCO_2$. In some aspects of the technology, the preheating element 354 may be a heating coil made from metal, ceramic, or other material capable of heating the one or more disinfectant lines 307 up to at least 60° C. In some embodiments, controllable preheating element 354 may be operably attached to the removable cap 112. In such embodiments, the removable cap 112 may be configured to attach to, and detach from, the container 101 without disrupting the operability of the controllable preheating element 354. For example, the removable cap 112 may comprise a pocket made from a heat resistant material, such as fiberglass, to house the controllable preheating element 354.

In embodiments, the controllable preheating element 354 is operably connected to the automatic controller 311 wherein the controllable preheating element 354 is controlled automatically by the automatic controller 311 based on signals received from the one or more sensors 318. In some embodiments, the controllable preheating element 354 is operably connected to the manual temperature controller 310 and may be controlled and monitored manually by the user.

Any of the devices described in Example 3 may be used in various methods for the decontamination of contagious and/or biohazardous samples, including any of the decontamination co-solvents described in Bennet et al., *Evaluation of Supercritical $CO_2$ Sterilization Efficacy for Sanitizing Personal Protective Equipment from the Coronavirus SARS-CoV-2*, Elsevier, 18 Mar. 2021 and/or Bernhardt et al., *Improved Sterilization of Sensitive Biomaterials with Supercritical Carbon Dioxide at Low Temperature*, PLOS One, Jun. 12, 2015 specifically incorporated by reference herein. For example, in some embodiments, a method for decontaminating a contagious material prior to a hazardous release for medical and/or nonmedical applications may comprise a user providing the portable biocontainment device, such as the devices 300, 350 illustrated in FIGS. 3A and 3B. In some embodiments, medical applications may include analysis for diagnostic and/or therapeutic purposes through biomarker analysis, dehydration marker analysis, dehydration analysis, respiratory infection markers analysis, or environmental exposure to a chemical, biological, radiological, nuclear and/or explosive (CBRNE) agent analysis. Nonmedical applications may include decontaminating a non-biological sample before nonmedical research applications in a laboratory.

The method may also comprise collecting the contagious material to be decontaminated into the portable biocontainment device. In some embodiments, the contagious material may comprise pathogens to be sterilized. The contagious material may be liquid-phase or gas-phase biological sample such as OF, blood, urine, or EB. The contagious material may contain pathogens such as viruses, bacteria, fungi, protozoa, worms, or any combination thereof. The collection step may be facilitated by the user directly placing their mouth on the gas-phase opening 106 and expelling a fluid biological sample into the fluid port 104 wherein the fluid biological sample flows through the liquid biological sample inlet 108 and into the container reservoir 102. The collection step may also be facilitated by the user absorbing a liquid sample in the compressible absorbent pad 156 and inserting the insertable liquid collector 150 into the insert port 160 as illustrated in FIG. 2 wherein the liquid sample flows through the liquid biological sample inlet 108 and into the container reservoir 102. The collection step may also be facilitated by the user pouring or injecting a sample into the gas-phase opening 106 wherein the sample flows through the liquid biological sample inlet 108 and into the container reservoir 102.

The method also comprises introducing a specified amount of the $CO_2$ to the portable biocontainment device. The introduction of $CO_2$ step is preferably facilitated by the automatic controller 311. In other embodiments, the user may manually introduce the $CO_2$ by adjusting the manual disinfectant controller 308. In preferred embodiments, the $CO_2$ is introduced in its liquid phase to allow for the transition from liquid phase $CO_2$ into the $CO_2$ supercritical state. In some embodiments, such as the device illustrated in FIG. 3A, the $CO_2$ is introduced to the pressure vessel volume 303. In other embodiments, such as the device illustrated in FIG. 3B, the $CO_2$ is introduced to the container reservoir 102. The specified amount of $CO_2$ may be optimized depending on the volume of the decontamination location 303, 102 and/or the amount of sample present.

To create an environment suitable for the transformation of the $CO_2$ to its supercritical state, the method may further comprise adjusting the pressure and temperature within the portable biocontainment device to at least 1500 psi and 31° C. to 60° C., respectively. The adjusting the pressure may be controlled and monitored by the exhaust controller 316 and the pressure sensor 312, respectively. In aspects of the technology, the adjusting the pressure step may be controlled by the automatic controller 311 by engaging the controllable heating element 304 (FIG. 3A) or the controllable preheating element 354 (FIG. 3B) to increase its temperature and thereby increase the temperature and pressure of the decontamination location 303, 102. Similarly, the adjusting temperature within the portable biocontainment device may be controlled and monitored by the automatic controller 311. In this manner, the adjusting the pressure and temperature is performed automatically based on the communications received by the automatic controller 311 from the one or more sensors 318. Of course, the adjusting the pressure and temperature step may also be performed manually by engaging the manual temperature controller 308, the exhaust controller 316, and/or the automatic controller 311.

To increase the likelihood of decontamination, the method may further comprise maintaining the suitable device environment for 10 to 60 minutes. To facilitate the maintaining the suitable device environment, the automatic controller 311 may be programmed to hold the pressure and temperature described in the adjusting the pressure and temperature step for a predetermined amount of time. The predetermined amount of time may be optimized depending on the suspected contagious samples in the portable biocontainment device. For example, some bacterial endospores may be inactivated in about 40 minutes. The maintaining the pressure step may also include pressure cycling (pressurizing and depressurizing) in order to increase the efficacy of the decontamination of the contagious samples. In embodiments, the automatic controller 311 may be programmed to run the pressure cycling. Of course, the maintaining the suitable device environment may also be performed manually by the user setting a timer for the predetermined time. To facilitate manual pressure cycling, the user may adjust the manual temperature controller 310 and/or the exhaust controller 316 on a set schedule.

Optionally, the method may further comprise introducing a specified amount of the disinfectant additive to the portable biocontainment device. In embodiments, the introduction of the disinfectant additive step is facilitated by the automatic controller 311 configured to control the flowrate of the disinfectant additive into the portable biocontainment device after receiving signals of the predetermined threshold from the one or more sensors 318. In other embodiments, the introduction of the disinfectant additive step may be facilitated by the manual disinfectant controller 308 wherein the user may manually adjust the flowrate of the disinfectant additive into the portable biocontainment device. In embodiments, the disinfectant additive is introduced in the liquid phase. In other embodiments, the disinfectant additive is the dehydrated liquid solution, such as in the dissolvable tablet or dried on a membrane, and is positioned in the area to be decontaminated. In other embodiments, the dehydrated disinfectant additive is positioned within the one or more disinfectant lines 307 wherein the flow of the $CO_2$ may dissolve the dehydrated disinfectant additive. In some embodiments, such as the device illustrated in FIG. 3A, the disinfectant additive is introduced to the pressure vessel volume 303. In other embodiments, such as the device illustrated in FIG. 3B, the disinfectant additive is introduced to the container reservoir 102. The specified amount of the disinfectant additive may be optimized depending on the volume of a decontamination location (i.e., the pressure vessel volume 303 as illustrated in FIG. 3A or the container reservoir 102 as illustrated in FIG. 3B), the amount of sample present, the type of sample, and/or the desired level of disinfection.

Example 4: Collecting & Transporting One or More Viable Biological Samples

Referring to FIGS. 4A-4B, the devices provided herein are useful in various collection and transport methods. As summarized by the flowchart in FIG. 4A, the user may employ the following method to collect one or more viable biological samples. In some embodiments, the method comprises a user providing any of the portable biocontainment devices 400 described herein, such as the devices illustrated in FIG. 1A, FIG. 2, FIG. 3A, and FIG. 3B. The method may also comprise introducing the liquid-phase biological sample 121, 402 into the liquid biological sample inlet 108. The introducing step 402 may be performed by inserting a biological liquid, such as OF or blood, into the fluid port 104 via the one or more openings, such as the gas-phase opening 106 and/or the liquid-phase opening 158 as illustrated in FIG. 2 (and also FIG. 1A, FIG. 3A, and FIG. 3B). In some embodiments where an OF sample is collected, the user may place the gas-phase opening 106 of the fluid port 104 directly to their mouth and expel the OF. In other embodiments, the user may use a syringe or a similar device to insert the liquid-phase biological sample 121 to the one or more openings of the fluid port 104 to introduce the liquid-phase biological inlet 108. In other embodiments, the user may use the insertable liquid collector 150 to introduce the liquid-phase biological sample 121 into the liquid biological sample inlet 108. The method may also comprise collecting the liquid-phase biological sample, 121, 404 into the liquid sample container 120 thereby storing one or more viable biological samples 414.

In embodiments, the method may also comprise introducing the gas-phase biological sample 406 into the gas biological sample inlet 110. In some embodiments, the introducing the gas-phase biological sample 406 may be performed by inserting a gas-phase sample, such as EB, into the fluid port 104 via the gas-phase opening 106 as illustrated in FIG. 1A (and also FIG. 2, FIG. 3A, and FIG. 3B). In some embodiments where an EB sample is collected, the user may place the gas-phase opening 106 of the fluid port 104 directly to their mouth and expel the EB. The method may also comprise condensing the gas-phase biological sample to the condensed liquid sample 127, 408. The condensing step may be performed by the condensing spiral tube 122 illustrated in FIGS. 1A, 2, 3A, and 3B. The method also comprises collecting the condensed liquid sample 127 into the condensation sample container 126, 410 thereby storing one or more viable biological samples 414.

Optionally, the method may also comprise cooling the sample container(s) and/or collection components 412 used in the collecting the liquid-phase biological sample 404 and/or collecting the condensed liquid sample 410 step(s) by introducing the cooling element 128 to the cooling chamber 130 thereby securing one or more viable biological samples 414. As desired, the methods and devices may incorporate a heating element, such as a heater, in thermal contact with the collected samples. In this manner, heat may be employed if the collected samples fall below a user-defined cut-off. This can be of importance where the shipped devices are in a cold environment and it is desired to avoid freezing of the collected samples. Both cooling and heating may be provided to ensure a robust temperature control over a wide range of temperatures, including external environment conditions that are from below freezing (less than 0° C.) to above body temperature (greater than 37° C.).

FIG. 4B illustrates further aspects of the technology. In some embodiments, the user may also complete the step of shipping the one or more biological samples to a remote testing facility 450. In some examples, the shipping is by a commercial service provider, such as FedEx® or UPS®, and/or the shipping is performed by a drone 452. The shipping by the commercial service provider may be by an automobile, a train, a plane, a drone, or any other mode of transportation employed by the commercial service provider. In some embodiments, the portable biocontainment device may be placed in an additional storage container configured to safely transport the device to the remote testing facility. For example, such additional storage container may be a device described in any of the storage containers provided in PCT Pub. No. WO 2020/118085 titled "Smart Storage Container for Health Logistics".

In embodiments, the biological samples may remain viable and safely contained in a variety of shipping conditions. The shipping condition may be a shipping time period of up to 28 hours and up to 4 days with a stabilizer in the sample container 120, 126, 454. For example, the shipping condition may be a shipping time period of up to 24 hours if the stabilizer is not placed in the sample container 120, 126. In other examples, the shipping time period may be up to 3 days when the stabilizer is placed in the sample container 120, 126. The stabilizer may be in the form of a dried pellet positioned within the liquid sample container 120 and/or the condensation sample container 126 that is configured to dissolve when a sample is collected in the sample containers 120, 126. The stabilizer may also be in the form of a liquid positioned within the liquid sample container 120 and/or the condensation sample container 126.

In other embodiments, the shipping condition may be a temperature range from −60° C. to 60° C. with selectably controlled temperature of the sample containers 454, 120, 126. For example, the shipping condition may be a temperature range from −40° C. to 50° C. In this manner, the temperature of the sample container(s) 120, 126 may be controlled depending on the analyte of interest. The analyte of interest may range from protein, lipid, volatile organic compounds, or microbiota. In examples, the selectably controlled temperature of the sample containers 120, 126 may be controlled by the cooling element 128 as shown in FIG. 1A.

In other examples, the shipping condition may be an impact or shock force against the device 454. The impact or shock force against the device may be caused by a carrier or drone dropping the device.

In other embodiments, the biological samples may remain viable and safe in a shipping condition of a humidity range of between 1% to 100% humidity 454.

Each of the above-described shipping conditions 454, time, temperature, impact force, and humidity, may occur independently or in any combination thereof. Provided that the shipping conditions fall within the above-described shipping conditions 454, the method comprises delivering the biological samples to the remote facility for analysis 458. Of course, if an individual at the remote facility visually observes that the biological samples have been compromised, i.e., a leak, despite the shipping conditions falling within the above-described parameters, the individual may manually implement device decontamination procedures 458. For example, if the provided portable biocontainment device from the providing step 400 is the ambient pressure two-in-one device 100, the individual may proceed with the remote facility's decontamination protocols to decontaminate the device.

If the shipping conditions fall outside of the above-described parameters, the individual may also manually implement device decontamination procedures 458. For example, if the provided portable biocontainment device from the providing step 400 is the targeted disinfectant dispersal device 300 or the non-targeted disinfectant dispersal device 350 the individual may visually inspect the provided device to see if any of the fail-safe features have been implemented. If not, and the biological samples have been compromised, the individual may manually engage the fail-safe mechanisms described in Example 3 to decontaminate the provided device, such as by manually adjusting a controller 311 to increase the flowrate of disinfectant into the device. In an embodiment, the decontamination step 458 may also be automatically employed through the use of an electronic controller, such as an automatic controller 311, operably connected to one or more sensors that monitor one or more shipping conditions. For example, a force sensor may detect severe physical forces on the device, such as associated with high impact force from a fall, with the resultant signal transmitted to a processor of the electronic controller that results in actuation of an electronically-controlled valve that releases $scCO_2$ or $scCO_2$ and the disinfectant additive to decontaminate the device. In a similar manner, any other of the monitored shipping conditions can be used to automatically decontaminate the device for a condition that exceeds a user-defined within tolerance operating condition.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Every device, system, formulation, combination of components, or method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A portable biocontainment device for collecting and storing a hazardous or an infectious agent comprising:
 a container having a side wall, a bottom wall and a top wall to define a container reservoir;
 a fluid port traversing the side wall of the container and extending between the container reservoir and an external environment outside the container reservoir, the fluid port comprising:
  one or more openings configured to receive a liquid-phase biological sample and/or a gas-phase biological sample;
  a gas biological sample inlet;
  a liquid biological sample inlet;
  wherein the one or more openings are externally positioned relative to the container reservoir and each of the gas biological sample inlet and the liquid biological sample inlet is posit a condensing spiral tube positioned in the container reservoir and having a spiral tube proximal end fluidically connected to the gas biological sample inlet;

a condensation sample container fluidically connected to a distal end of the condensing spiral tube for storing a condensed liquid sample from the gas-phase biological sample;

a tube positioned in the container reservoir and having a tube proximal end fluidically connected to the liquid biological sample inlet; and a liquid sample container fluidically connected to a distal end of the tube for storing a liquid sample from the liquid-phase biological sample.

2. The portable biocontainment device of claim 1, further comprising:
a cooling chamber positioned in the container reservoir configured to receive a cooling element, wherein the cooling chamber is in thermal contact with the condensing spiral tube.

3. The portable biocontainment device of claim 2, wherein the cooling chamber is in thermal contact with the condensation sample container and the liquid sample container.

4. The portable biocontainment device of claim 1, wherein the top wall of the container is a removable cap that is configured for removal to position the cooling element in the cooling chamber and/or to connect the portable biocontainment device to a biocontainment handling component for biocontainment during sample handling.

5. The portable biocontainment device of claim 1, wherein the one or more openings comprise a gas-phase opening and a liquid-phase opening, further comprising:
an insertable liquid collector;
an insert port extending between the liquid-phase opening and the liquid biological sample inlet, wherein the insert port is configured to receive the insertable liquid collector.

6. The portable biocontainment device of claim 5, wherein the insertable liquid collector comprises:
a compressible absorbent pad having a longitudinal axis extending between a first end and a second end;
a liquid indicator aligned with the compressible absorbent pad longitudinal axis;
a hand bar, having a proximal end connected to the compressible absorbent pad second end and/or the liquid indicator;
wherein the compressible absorbent pad is configured for insertion into the insert port and the hand bar is accessible to a subject to control compression of the compressible absorbent pad in the insert port.

7. The portable biocontainment device of claim 5, wherein the insertable liquid collector comprises:
a compressible absorbent pad having a longitudinal axis extending between a first end and a second end;
a removable liquid collection conduit, having a distal end configured to fluidically connect to the liquid biological sample inlet;
a liquid indicator aligned with the compressible absorbent pad longitudinal axis;
a hand bar, having a proximal end connected to the compressible absorbent pad second end and/or the liquid indicator;
a plurality of apertures positioned through the insert port for conveying liquid sample from the gas-phase opening to the liquid biological sample inlet;
wherein the compressible absorbent pad is configured for insertion into the removable liquid collection conduit and the hand bar is accessible to a subject to control compression of the compressible absorbent pad in the insert port.

8. The portable biocontainment device of claim 1, further comprising an excess liquid collection container connected to the fluid port to collect excess liquid from the introduced liquid-phase biological sample.

9. The portable biocontainment device of claim 1, configured for safe transportation of a biohazardous sample under a range of ambient environmental conditions and/or a range of transport times, including up to 28 hours.

10. The portable biocontainment device of claim 1, wherein the container reservoir is pressurizable to a negative pressure, wherein the negative pressure is generated in the container reservoir by a pressure pump assembly operably connected to the container reservoir.

11. The portable biocontainment device of claim 10, wherein the pressure pump assembly comprises:
a spring to remove air from the container reservoir;
a vent between the container reservoir and external environment having an open vent configuration for air removal from the container reservoir during pump operation and a close vent configuration to maintain the negative pressure in the container reservoir; and
a filter between the container reservoir and the external environment to prevent release of a biological agent to the external environment.

12. The portable biocontainment device of claim 1, wherein the liquid biological sample inlet receives an oral fluid and/or the gas biological sample inlet receives an exhaled breath from a patient to-be-tested for a symptom of the infectious agent, including a biomarker of the infectious agent.

13. The portable biocontainment device of claim 1, further comprising a filtration system positioned between the liquid biological sample inlet and the tube to filter the liquid-phase biological sample.

14. The portable biocontainment device of claim 1, wherein during biocontainment storage the infectious agent in the liquid sample container and/or the condensation sample container remains viable.

15. The portable biocontainment device of claim 1, wherein a collected sample is used for any one or more of:
biomarker analysis from a biological fluid sample, including saliva, sputum, plasma, blood, urine, amniotic fluid, bone marrow, breast milk, synovial fluid, semen, vaginal fluid, mucus, or lymph;
exhaled breath biomarker analysis;
noninvasive based dehydration marker analysis;
microbiota analysis;
dehydration analysis;
respiratory infection markers analysis;
environmental exposure to a chemical, biological, radiological, nuclear and/or explosive (CBRNE) agent; or
a diagnostic assay at a remote facility for detecting one or more of a virus, bacteria, fungus and/or a polynucleotide sequence (e.g., DNA and/or RNA).

16. The portable biocontainment device of claim 1, further comprising a targeted decontamination device operably connected to the container comprising:
one or more disinfectant lines having a disinfectant line proximal end and a disinfectant line distal end;
one or more disinfectant storage containers operably connected to the disinfectant line proximal end, wherein at least one of the one or more disinfectant storage containers is configured to store $CO_2$;

a controller connected to the one or more disinfectant lines to control a flowrate of a disinfectant from the one or more disinfectant storage containers through the one or more disinfectant lines;

a pressure vessel, operably connected to the disinfectant line distal end, defining a pressure vessel volume, wherein the liquid sample container and the condensation sample container are positioned within the pressure vessel volume;

a controllable heating element positioned within the pressure vessel volume;

a pressure sensor operably connected to the pressure vessel;

an exhaust line having an exhaust line proximal end and an exhaust line distal end wherein the pressure vessel is operably connected to the exhaust line proximal end and the exhaust line distal end opens to the external environment;

an exhaust controller connected to the exhaust line to control a flowrate of gas from the pressure vessel volume to the external environment;

wherein the pressure vessel is configured to contain pressure levels up to 2500 psi and temperature levels up to 60° C. for a period of between 10 minutes to 60 minutes configured for the $CO_2$ transformation to supercritical $CO_2$ ($scCO_2$) in the pressure vessel volume to sterilize any contagion accessible to the $scCO_2$.

17. The portable biocontainment device of claim 1, further comprising a non-targeted decontamination device operably connected to the container comprising:

one or more disinfectant lines having a disinfectant line proximal end and a disinfectant line distal end;

one or more disinfectant storage containers operably connected to the disinfectant line proximal end wherein at least one of the one or more disinfectant storage containers is configured to store $CO_2$;

a controller connected to the one or more disinfectant lines to control a flowrate of a disinfectant from the one or more disinfectant storage containers through the one or more disinfectant lines;

a controllable preheating element wherein at least a portion of the one or more disinfectant lines traverses the controllable preheating element to heat the disinfectant flowing through the one or more disinfectant lines;

the disinfectant line distal end configured to open to the container reservoir;

a pressure sensor operably connected to the container reservoir;

an exhaust line having an exhaust line proximal end and an exhaust line distal end wherein the container reservoir is operably connected to the exhaust line proximal end and the exhaust line distal end opens to the external environment;

an exhaust controller connected to the exhaust line to control a flowrate of gas from the container reservoir to the external environment;

wherein the side wall, the bottom wall and the top wall of the container are configured to contain pressure levels up to 2500 psi and temperature levels up to 60° C. for a period of between 10 minutes to 60 minutes configured for the $CO_2$ transformation to supercritical $CO_2$ ($scCO_2$) in the container reservoir to sterilize any contagion accessible to the $scCO_2$.

18. A method of storing one or more viable biological samples, the method comprising the steps of:

providing the portable biocontainment device of claim 1;
introducing:
the liquid-phase biological sample into the liquid biological sample inlet; and
the gas-phase biological sample into the gas biological sample inlet;

collecting the liquid-phase biological sample into the liquid sample container;

condensing at least a portion of the gas-phase biological sample in the condensing spiral tube to the condensed liquid sample;

collecting the condensed liquid sample into the condensation sample container;

thereby storing one or more viable biological samples.

19. The method of claim 18, further comprising the steps of:

introducing the cooling element to the cooling chamber; and cooling the liquid sample container and the condensation sample container and/or collection components with the introduced cooling element.

20. The method of claim 18, wherein the one or more viable biological samples remain viable and contained for a shipping condition, wherein the shipping condition is selected from the group consisting of:

a shipping time period of up to 28 hours or up to 4 days with a stabilizer in the sample container;

a temperature variation ranging from −60° C. to 60° C., with the temperature of the sample container selectably controlled depending on the one or more viable biological samples, wherein the one or more viable biological samples comprise of one or more of a protein, a lipid, a volatile organic compound, or microbiota;

an impact or shock force exerted against the portable biocontainment device; and a humidity range of between 1% to 100% humidity.

21. A method for decontaminating a contagious material the method comprising the steps of:

providing the portable biocontainment device of claim 16;

collecting the contagious material to be decontaminated into the portable biocontainment device;

introducing the $CO_2$ to the portable biocontainment device;

adjusting the pressure and temperature within the portable biocontainment device to at least 1500 psi and 31° C. to 60° C., respectively, for supercritical transformation of the $CO_2$; and maintaining the pressure and temperature levels for 10 to 60 minutes;

thereby decontaminating the contagious material.

22. The method of claim 21, wherein the method further comprises introducing the disinfectant to the portable biocontainment device.

* * * * *